United States Patent [19]
Tuomanen et al.

[11] Patent Number: 5,834,278
[45] Date of Patent: Nov. 10, 1998

[54] BACTERIAL PEPTIDE METHIONINE SULFOXIDE REDUCTASE AN ADHESION-ASSOCIATED PROTEIN, AND ANTIBIOTIC THERAPIES BASED THEREON

[75] Inventors: Elaine Tuomanen; H. Robert Masure; Theresa M. Wizemann, all of New York, N.Y.

[73] Assignee: The Rockefeller University, New York, N.Y.

[21] Appl. No.: 642,247

[22] Filed: May 1, 1996

[51] Int. Cl.[6] .............................. C12N 9/02; C12N 1/20; C07H 21/04; C12P 21/06
[52] U.S. Cl. ................ 435/189; 536/23.2; 536/23.7; 435/69.1; 435/252.3; 435/320.1; 435/885; 530/350; 530/412
[58] Field of Search .................... 435/189, 69.1, 435/252.3, 320.1, 885; 536/23.2, 23.7; 530/350, 412

[56] References Cited

U.S. PATENT DOCUMENTS 5,455,240 10/1995 Tuomanen et al. ................... 514/210

FOREIGN PATENT DOCUMENTS

WO 95/06732 3/1995 WIPO .

OTHER PUBLICATIONS

Rahman et al. (1992). J. Biol. Che. 267(22):15549–51. Aug. 5, 1992.
Moskovitz et al. (1996) PNAS 93:2095–99. 1996.
Arvidson and So, *J. Biol Chem,* 270:26045–26048 (1995).
Arvidson and So, *J. Bacteriol,* 177:2497–2504 (1995).
Cundell, et al., *Infect Immun,* 63, 757–761 (1995).
Cundell et al., *Nature,* 377:435–438 (1995).
Cundell et al., *Infect. Immun.* 63:2493–2498 (1995).
Fleischmann, R.D., et al. *Science,* 269:496–512 (1995).
Fraser et al., *Science,* 270:397–403 (1995).
Jones et al., *Proc. Natl. Acad. Sci. USA,* 92:2081–2085 (1995).
Taha and Giorgini, *Mol Microbiol,* 15:667–77 (1995).
Freedman et al. (1994) TIBS 19:331.
Vargas et al., *J. Bacteriol,* 176:4117–23 (1994).
Wilson et al. (1994) *Nature* 369:32–8.
Brot and Weissbach, *Arch. Biochem. Biophys.,* 223: 271–281 (1993).
Dupuy et al., *J. Biol Chem,* 266:3739–43 (1992).
Martin et al., *Nucleic Acids Res.,* 20:3479–3483 (1992).
Rahman et al., *Cell. Mol. Biol.* 38:529–542 (1992).
Rahman et al., *J. Biol. Chem.,* 267:15549–15551 (1992).
Taha et al., *J. Bacteriol.* 174:5978–5981 (1992).
Taha et al., *Mol. Microbiol* 5:137–48 (1991).
Pille et al., *J. Bacteriol,* 172:1556–1561 (1990).
Brot and Weissbach, in *The Chemistry of Sulphones and Sulphoxides,* p. 851–872 (1988).
Taha et al., *EMBO J.* 7:4367–4378 (1988).
Christman et al., *Cell,* 41:753–762 (1985).
Abrams et al., *Proc. Natl. Acad. Sci. USA* 78:7483–7486 (1981).
Brot et al., *Proc. Natl. Acad. Sci. USA* 78:2155–2158 (1981).

*Primary Examiner*—Robert A. Wax
*Assistant Examiner*—Tekchand Saidha
*Attorney, Agent, or Firm*—Klauber & Jackson

[57] ABSTRACT

The present invention relates to the identification of a bacterial adhesion associated protein, and the gene encoding such protein. More particularly, the invention relates to a pneumococcal peptide methionine sulfoxide reductase involved in bacterial adherence. The invention also relates to identification and development of agents to provide protection from bacterial infection based on this protein.

The invention provides nucleic acids encoding the peptide methionine sulfoxide reductase, as well as methods for identifying antagonists of the methionine sulfoxide reductase. The present invention further demonstrates that peptide methionine sulfoxide reductase is an adhesion-associated protein in various Gram-negative and Gram-positive bacteria and accordingly provides for interference with the peptide methionine sulfoxide reductase to inhibit bacterial adherence to host tissues.

9 Claims, 7 Drawing Sheets

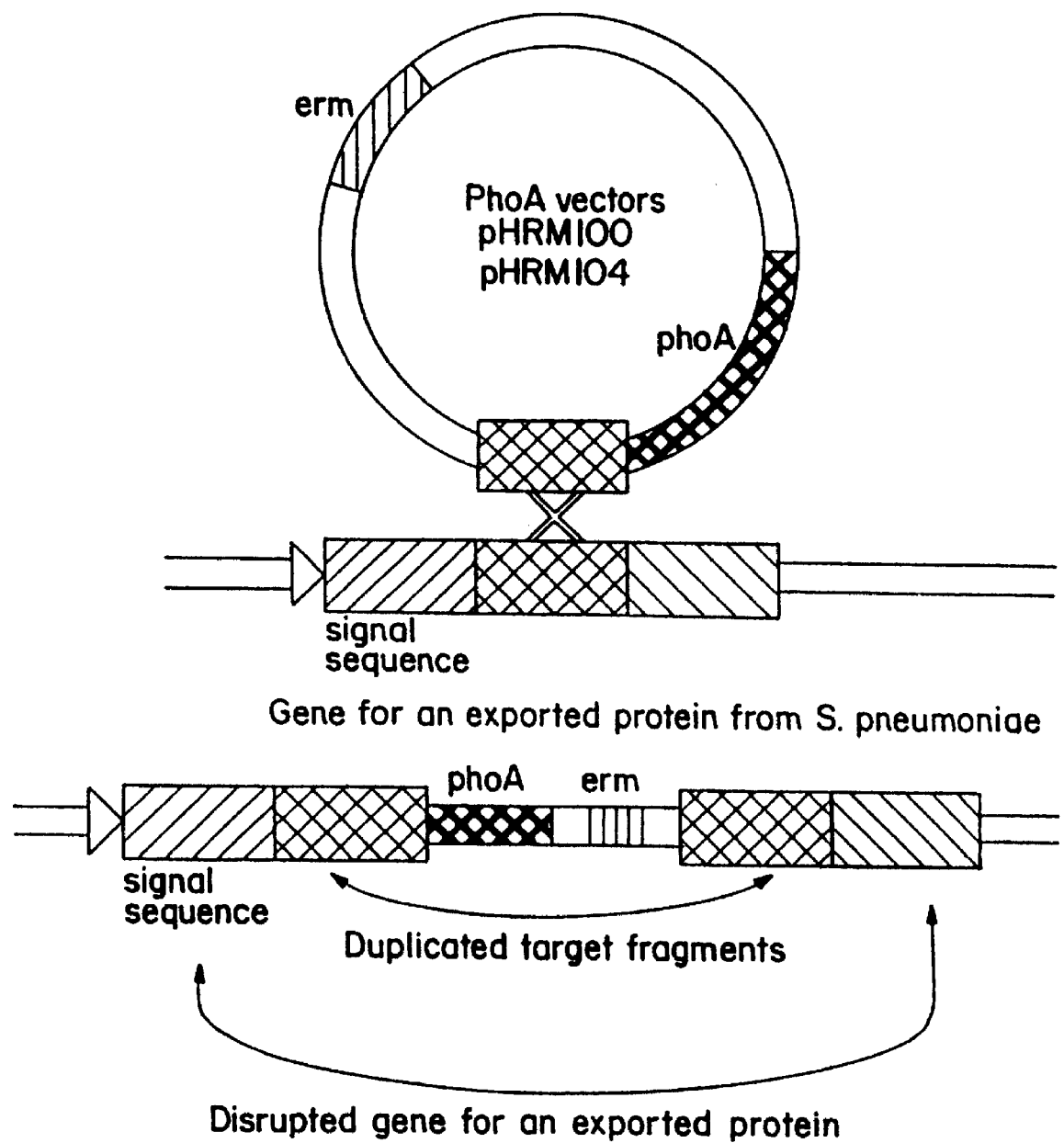

FIG. 4B

```
              1                                                          50
PilB          mkhrtffslc akfgcllalg acspkivdag tatvphtlst lktadnrpas
              .......... .......... .......... .......... ..........
              .......... .......... .......... .......... ..........
Consensus     ---------- ---------- ---------- ---------- ----------

51                                                        100
PilB          vylKkDkPtL ikFWAsWCPl ClsElgqaEK wAqdakfssa nlitvaspgf
DsbE          .64qqgePvL lnvWAtWCPt CyaEhqyLnK LAKE94.... ..........
TrxA          .17KsDvPvv vdFWAeWCgp CrqigpaLEe LsKE48.... ..........
Consensus     ---K-D-P-L --FWA-WCP- C--E---LEK LAKE------ ----------

101                                                       150
PilB          lhekkdgefq kwyaglnypk lpvvtdnggt iaqnlniSvY pswaLIgkdg
              .......... .......... .......... .......... ..........
MsrA          .......... .......... .......... ......mSlF dkkhLVspad
Consensus     ---------- ---------- ---------- -------S-- ----L-----

151                                                       200
PilB          dvqrivkgsi neaqalalir nPnadlgslk hsFykpdtqk kdsaimntrt
pMsrA         .......... .......... .......... .......... .......Mae
MsrA          al........ .......... .Pgrntpmpv atLhavnghs mtnvpdgMei
Consensus     ---------- ---------- -P-------- ---------- -------M--

201                                                       250
PilB          IYLAaaasga wkp.iSnaSt aWlTryrYAN GnTENPsYeD VsyrhTGHAE
pMsrA         IYLAgGCFWG lEeyFSriSG VleTsgGYAN GqvEttnYql le..ETdHAE
MsrA          aiFAmGCFWG vErlFwqlpG VYsTaaGYtg GyTpNPtYrE VcsgDTGHAE
Consensus     IYLA-GCFWG -E--FS--SG V--T--GYAN G-TENP-Y-- V----TGHAE 251                                                       300
PilB          tVkVtYDadk lSLDDILQYY FRVVDPtSlN kQGNDtGTQY RSGVYYtDPA
pMsrA         AVRVICDekg VSLrEILlYY FRVIDPlSiN qQGNDrGrQY RtGIYYqDeA
MsrA          AVRIVYDpsv ISyEqlLQvF WenhDPaqgm rQGNDhGTQY RSaIYpltPe
Consensus     AVRV-YD--- -SL--ILQYY FRV-DP-S-N -QGND-GTQY RSGIYY-DPA 301                                                       350
PilB          EkAvIaAaLk ReQqky.... .qlplvVEnE pLknFYdAEE YHQDYLiKNP
pMsrA         DlpAIytvvq eqermL.... .gRkIaVEVE qLrhYilAED YHQDYLrKNP
MsrA          qdAAarAsLe RfQaaMlaad ddRhIttEIa natpFYyAED dHQqYLhKNP
Consensus     --AAI-A-L- R-Q------- --R-I-VE-E -L--FY-AED YHQDYL-KNP 351                                                       400
PilB          nGYCHIDIrk ADePLPgktk aapqgQrlrr gqriKnrvtp nSnapdrrai
pMsrA         sGYCHIDVtd ADkPLidaAn yekpsQev.. ...lKaslse eS.......y
MsrA          yGYC..gIgg igvcLPpeA. .......... .......... ..........
Consensus     -GYCHIDI-- AD-PLP--A- -----Q---- ----K----- -S--------

401                                                       450
PilB          psdQnsATEy aFsheYDhlF kpGIYVDVvs GEPLFssaDK YdSGCGWPSF
pMsrA         rvtQeaATEa pFtnaYDqtF eeGIYVDItt GEPLFfakDK FaSGCGWPSF
MsrA          .......... .......... .......... .......... ..........
Consensus     ---Q--ATE- -F---YD--F --GIYVD--- GEPLF---DK --SGCGWPSF 451                                                       500
PilB          tRPIdaksVt ehdDFSfnMr RtEVRSRaad sHLGHVFpDG PRDkGGLRYC
pMsrA         sRPIskellh yykDLShgMe RiEVRSRsgs aHLGHVFtDG PRElGGLRYC
MsrA          .......... .......... .......... .......... ..........
Consensus     -RPI------ ---D-S--M- R-EVRSR--- -HLGHVF-DG PR--GGLRYC 501             527
PilB          INgASLkFIp lEqMDaAGYG aLkgevk
pMsrA         INsASLrFVa kDeMEkAGYG yLlpyln
MsrA          .......... .......... .......
Consensus     IN-ASL-F-- ---M--AGYG -L-----
```

BACTERIAL PEPTIDE METHIONINE SULFOXIDE REDUCTASE AN ADHESION-ASSOCIATED PROTEIN, AND ANTIBIOTIC THERAPIES BASED THEREON

The research leading to the present invention was supported in part by the United States Government, Grant Nos. AI27913 and AI36445. The Government may have certain rights in the invention.

FIELD OF THE INVENTION

The present invention relates to the identification of a bacterial adhesion associated protein, and the gene encoding such protein. More particularly, the invention relates to a pneumococcal peptide methionine sulfoxide reductase involved in bacterial adherence. The invention also relates to identification and development of agents to provide protection from bacterial infection based on this protein.

BACKGROUND OF THE INVENTION

Many proteins in bacteria participate in diverse and essential cell functions such as motility, signal transduction, macromolecular transport and assembly, and the acquisition of essential nutrients. A number of protein functions are critical to these activities, though the proteins do not mediate the activities directly. Rather, they are integral to the pathway of bacterial virulence, as intermediates in the synthesis of bacterial cell walls, for example.

Pathogenic bacteria rely on adhesins to bind to host tissues. Cellular recognition and attachment of pathogenic microorganisms to eucaryotic cells mediated by surface exposed macromolecules are critical steps in the successful colonization and subsequent invasion of tissues in the human host [Ofek & Doyle in *Bacterial Adhesion to Cells and Tissues*, (Chapman & Hall, New York), p. 578. (1994)]. For example, the majority of isolates, including all pathogenic isolates, of *Escherichia coli* express rigid filamentous appendages, type I fimbriae, that mediate adherence to mannose containing glycoconjugates on the surfaces of eucaryotic cells [Jones et al., *Proc. Natl. Acad. Sci. USA*, 92:2081–2085 (1995); Abraham et al., *Nature*, 336:682–684 (1988)]. As another example, type IV pili and PII outer membrane proteins expressed on the surface of *N. gonorrhoea* mediate adherence, in a complex manner, to several classes of glycoconjugate-containing receptors on the surfaces of epithelial cells of the urogenital tract [Ofek and Doyle, 1994,supra; Deal and Krivan *J. Biol. Chem.*, 265:12774–12777 (1990)]. The interaction between adhesins expressed on the surface of *S. pneumoniae* and the ligands on type II lung cells (LC) and vascular endothelial cells (EC) has been studied in detail [Cundell et al., *Infect. Immun.* 63:2493–2498 (1995); Cundell and Tuomanen, *Microb. Pathog*, 17:361–374 (1994); Geelan et al., *Infect. Immun.*, 61:1538–1543 (1993)]. *S. pneumoniae* recognize three classes of glycoconjugate-containing receptors on the surfaces of LC and EC. Pneumococci bind to glycoconjugate receptors containing the disaccharides GalNAcβ1-3Gal or GalNAcβ1-4Gal. A third receptor containing GlcNAc is expressed after these cells are treated with several pro inflammatory agents and it is likely that this is the PAF (platelet activating factor) receptor [Cundell et al., *Nature*, 377:435–438 (1995)]. The maintenance of the functional properties of these extracellular molecules is essential for the pathogenicity of these microorganisms.

A strategy for the genetic analysis of exported proteins in *E. coli* was suggested following the description of translational fusions to a truncated gene for alkaline phosphatase (phoA) that lacked a functional signal sequence (Hoffman and Wright, 1985, Proc. Natl. Acad. Sci. U.S.A. 82:5107–5111). In this study, enzyme activity was readily detected in strains that had gene fusions between the coding regions of heterologous signal sequences and phoA indicating that translocation across the cytoplasmic membrane was required for enzyme activity. Subsequently, a modified transposon, TnphoA, was constructed to facilitate the rapid screening for translational gene fusions (Manoil and Beckwith, 1985,Proc. Natl. Acad. Sci. U.S.A. 82:8129–8133). This powerful tool has been modified and used in many Gram negative pathogens such as *Escherichia coli* (Guitierrez et al., 1987, J. Mol. Biol. 195:289–297), *Vibrio cholera* (Taylor et al., 1989, J. Bacteriol. 171:1870–1878), *Bordetella pertussis* (Finn et al., 1991, Infect Immun. 59:3273–9; Knapp and Mekalanos, 1988, J. Bacteriol. 170:5059–5066) and *Legionella pneumophila* (Albano et al., 1992, Mol. Microbiol. 6:1829–39), to yield a wealth of information from the identification and characterization of exported proteins. A similar strategy based on gene fusions to a truncated form of the gene for β-lactamase has been used to the same end [Broome-Sinith et al., *Mol. Microbiol.* 4:1637–1644 (1990)]. A direct strategy for mapping the topology of exported proteins has also been developed based on "sandwich" gene fusions to phoA [Ehrmann et al., 87:7574–7578 (1990)].

For a variety of reasons, the use of gene fusions as a genetic screen for exported proteins in Gram positive organisms had met with limited success. Plasmid vectors that will create two or three part translational fusions to genes for alkaline phosphatase, β-lactamase and a-amylase have been designed for *Bacillus subtilis* and *Lactococcus lacti* (Payne and Jackson, 1991, J. Bacteriol. 173:2278–82; Perez et al., 1992, Mol. Gen. Genet. 234:401–11; Smith et al., 1987, J. Bacteriol. 169:3321–3328; Smith et al., 1988, Gene 70:351–361). Gene fusions between phoA and the gene for protein A (spa) from *Staphylococcus aureus* have been used to determine the cellular localization of this protein (Schneewind et al., 1992, Cell. 70:267–81). In that study, however, enzyme activity for alkaline phosphatase was not reported.

Mutagenesis strategies in several streptococcal species have also been limited for several reasons. Efficient transposons similar to those that are the major tools to study Gram negative bacteria have not been developed for streptococcus. Insertion duplication mutagenesis with non-replicating plasmid vectors has been a successful alternative for *Streptococcus pneumoniae* (Chen and Morrison, 1988, Gene. 64:155–164; Morrison et al., 1984, J. Bacteriol. 159:870). This strategy has led to the mutagenesis, isolation and cloning of several pneumococcal genes (Alloing et al., 1989, Gene. 76:363–8; Berry et al., 1992, Microb. Pathog. 12:87–93; Hui and Morrison, 1991, J. Bacteriol. 173:372–81; Lacks and Greenberg, 1991, Gene. 104:11–7; Laible et al., 1989, Mol. Microbiol. 3:1337–48; Martin et al., 1992, J. Bacteriol. 174:4517–23; McDaniel et al., 1987, J. Exp. Med. 165:381–94; Prudhomme et al., 1989, J. Bacteriol. 171:5332–8; Prudhomme et al., 1991, J. Bacteriol. 173:7196–203; Puyet et al., 1989, J. Bacteriol. 171:2278–2286; Puyet et al., 1990, J. Mol. Biol. 213:727–38; Radnis et al., 1990, J. Bacteriol. 172:3669–74; Sicard et al., 1992, J. Bacteriol. 174:2412–5; Stassi et al., 1981, Proc. Natl. Acad. Sci. U.S.A. 78:7028–7032; Tomasz et al., 1988, J. Bacteriol. 170:5931–5934; Yother et al., 1992, J. Bacteriol. 174:610–8).

Recently, apparent fusion proteins containing PhoA were exported in species of Gram positive and Gram negative bacteria [Pearce and Masure, *Abstr. Gen. Meet. Am. Soc. Microbiol.* 92:127, abstract D-188(1992)]. This abstract reports insertion of pneumococcal DNA upstream from the *E. coli* phoA gene lacking its signal sequence and promoter in a shuttle vector capable of expression in both *E. coli* and *S. pneumoniae*, and suggests that similar pathways for the translocation of exported proteins across the plasma membranes must be found for both species of bacteria.

Pearce et al. [*Mol. Microbiol.* 9:1037 (1993)] developed a strategy to mutate and genetically identify putative exported proteins in *Streptococcus pneumoniae* by coupling the technique of mutagenesis with gene fusions to phoA. Vectors were created and used to screen pneumococcal DNA in *Escherichia coli* and *S. pneumoniae* for translational gene fusions to alkaline phosphatase (PhoA). This study identified several genetic loci that encode putative exported proteins. By similarity to the derived sequences from other genes from prokaryotic organisms these loci probably encode proteins that play a role in signal transduction, macromolecular transport and assembly, maintaining an intracellular chemiosmotic balance and nutrient acquisition. The putative exported proteins identified by these techniques were perceived as vaccine candidates. These results were the subject of International Patent Publication WO 95/06732 by Masure et al., published Mar. 9, 1995, and U.S. patent application Ser. No. 08/116,541, filed Sep. 1, 1993, and Ser. No. 08/245,511, filed May 18, 1994, all of which are specifically incorporated herein by reference in their entirety.

It has been discovered by the present inventors that putative exported proteins identified using the PhoA strategy may identify proteins that indirectly affect exported protein functions, thus making such proteins suitable targets for drug development strategies.

The citation of references herein shall not be construed as an admission that such references are prior art to the present invention.

SUMMARY OF THE INVENTION

The present invention concerns identification of a gene encoding an adhesion-associated protein in a Gram positive bacteria, and the protein encoded by such gene, termed herein an "adhesion-associated gene". In particular, the invention provides for isolation of a gene encoding a Gram positive bacterial peptide methionine sulfoxide reductase, which is an adhesion-associated protein, and thus provides the gene and protein encoded thereby. In a specific embodiment, the peptide methionine sulfoxide reductase is pneumococcal peptide methionine sulfoxide reductase.

In addition to providing the virulence associated protein, the present invention provides for recombinant preparation of such protein by expression of the isolated peptide methionine sulfoxide reductase gene of the invention. Thus, the invention provides for sufficient quantities of the protein for evaluation in drug discovery procedures, such as testing libraries of compounds for binding and inhibition of protein function.

The present invention advantageously provides for the identification of bacterial, preferably Gram positive, and particularly pneumococcal, virulence inhibitory agents, such as small molecule agonists and antagonists of the peptide methionine sulfoxide reductase virulence protein of the invention. As noted above, such agonists or antagonists are preferably identified using a recombinant protein of the invention to identify binding activity. Subsequently, the agonist or antagonist can be tested in an in vitro, ex vivo, or in vivo assay of the invention for antipneumococcal activity, and more particularly for loss of adherence using an adherence assay described herein.

As exemplified herein, identification of antagonists of the pneumococcal peptide methionine sulfoxide reductase of the invention has important implications for reducing virulence of Gram positive, and indeed, as demonstrated with *E. coli*, Gram negative bacteria. More particularly, the present invention unexpectedly demonstrates that peptide methionine sulfoxide reductase is a adhesion-associated protein in these bacteria, and that knocking out peptide methionine sulfoxide reductase activity (whether by mutation or, as described herein, by identification of an inhibitory or antagonist compound) reduces bacterial adhesion, and thus, virulence. In a specific embodiment, infra, an antagonist of pneumococcal peptide methionine sulfoxide reductase of the invention can be used to block adherence of the Gram positive bacterium *Neisseria gonorrhoea*; in another specific embodiment, the antagonist can be used to block adherence of the Gram positive bacterium *E. coli*.

In vitro assays of steps in pneumococcal disease include adherence and internalization to resting and activated cells of the nasopharynx, lung, peripheral and brain vascular endothelium, and PAF receptor transfectants. Additional assays include adherence to immobilized carbohydrates as receptor analogs, adherence to extracellular matrix, DNA transformation, and autolysis.

Ex vivo lung-blood and blood-brain bilayer models provide another model for evaluating the effect of a potential drug, that has been demonstrated to bind, and preferably to modify the function, of a virulence protein of the invention.

In vivo assays for effects of antibacterial agents discovered by the methods and using the protein and gene of the present invention include, but are not limited to, colonization of host target cells in rabbit and rat, pneumonia in rabbit, and meningitis in rabbit. Host target cells include nasopharyngeal, lung endothelial, or blood vessel epithelial cells.

Thus, it is an object of the present invention to provide a gene encoding a virulence protein of Gram positive bacteria, particularly *Streptococcus pneumoniae*.

It is a further object of the invention to provide for recombinant preparation of sufficient quantities of such protein for drug discovery and development.

Still another object of the invention is to identify inhibitors of Gram positive, and particularly pneumoccoal, virulence.

Yet a further object of the invention is to test candidate virulence inhibitory agents in in vitro assays, ex vivo models, and in vivo assays.

A specific object is the identification of a virulence inhibitory agent for an peptide methionine sulfoxide reductase, i.e., an agent that inhibits the activity of the peptide methionine sulfoxide reductase.

These and other objects of the present invention will be better understood by reference to the following Drawings and the Detailed Description.

DETAILED DESCRIPTION OF THE INVENTION

Figure 1A:
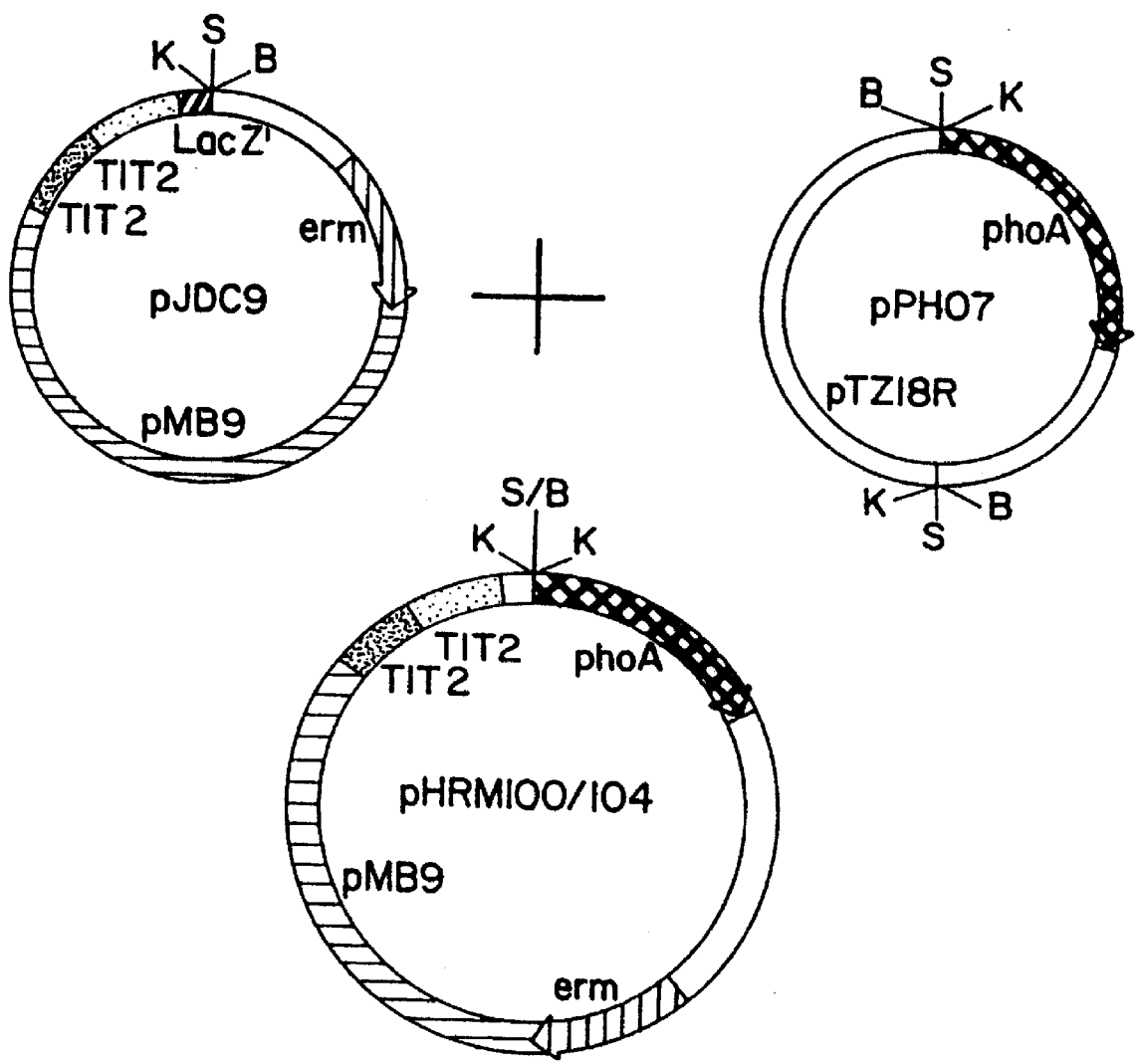
FIG. 1. Prior Art: Construction of PhoA fusion vectors designed for the mutation and genetic identification of exported proteins in *S. pneumoniae*. (A) The 2.6 kB fragment of pPHO7 containing a truncated form of phoA was inserted into either the SmaI or BamHI sites of pJDC9 to generate pHRM 100 and pHRM104 respectively. T1T2 are transcription terminators and the arrows indicate gene orientation. (B) Mechanism of insertion duplication mutagenesis coupled to gene fusion. PhoA activity depends on the cloning of an internal gene fragment that is in-frame and downstream from a gene that encodes an exported protein. Transformation into *S. pneumoniae* results in duplication of the target fragment and subsequent gene disruption.

As noted above, the present invention relates to the identification of a virulence protein, peptide methionine sulfoxide reductase, a gene encoding such protein, and the development of drugs that inhibit the activity of such virulence-associated protein. Advantageously, the peptide methionine sulfoxide reductase protein of the invention is an adhesion-associated protein.

The invention is based, in part, on the discovery that in vitro, ex vivo, and in vivo assays of mutant pneumococci provide for the identification of proteins that are involved in aspects of virulence. Such assays can particularly identify proteins that are involved in some aspect of adhesion, whether as adhesinis (see International Patent Publication No. WO 95/06732, published Mar. 9, 1995, U.S. patent application Ser. No. 08/116,541, filed Sep. 1, 1993, and U.S. patent application Ser. No. 08/245,511, filed May 18, 1994), or as adhesion accessory proteins, for example proteins that are involved in motility, signal transduction, cell wall assembly, glucose and energy metabolism, amino acid biosynthesis, molecular transport, or other aspects of adhesion.

In addition to providing a virulence, i.e., adhesion-associated, peptide methionine sulfoxide reductase, the present invention provides for recombinant preparation of such protein by expression of the isolated gene of the invention. Thus, the invention provides for sufficient quantities of peptide methionline sulfoxide reductase for evaluation in drug discovery procedures, such as testing libraries of compounds for binding and inhibition of the proteins enzymatic activity. More specifically, the present invention advantageously provides for the identification of bacterial, preferably Gram positive, particularly pneumococcal, virulence inhibitory agents, such as small molecule agonists and antagonists of the peptide methionine sulfoxide reductase of the invention. As noted above, such agonists or antagonists are preferably identified using recombinant protein of the invention to identify binding activity. Subsequently, the agonist or antagonist can be tested in an in vitro, ex vivo, or in vivo assay of the invention for bacterial, particularly pneumococcal, adherence.

In vitro assays of steps in pneumococcal disease include adherence and internalization to resting and activated cells of the nasopharynx, lung, peripheral and brain vascular endothelium, and PAF receptor transfectants. Additional assays include adherence to immobilized carbohydrates as receptor analogs, adherence to extracellular matrix, DNA transformation, and autolysis.

Ex vivo lung-blood and blood-brain bilayer models provide another model for evaluating the effect of a potential drug, that has been demonstrated to bind, and preferably to modify the function, of a virulence protein of the invention.

In vivo assays for effects of antibacterial agents discovered by the methods and using the proteins and genes of the present invention include, but are not limited to, colonization of host target cells in rabbit and rat, pneumonia in rabbit, and meningitis in rabbit. Host target cells include nasopharyngeal, lung endothelial, or blood vessel epithelial cells.

Adhesion assays can be performed on any eukaryotic cell line that serves as a host for the bacterium. Preferably, if infection of humans is important, the cell or cell line is derived from a human source or has been demonstrated to behave like human cells in a particular in vitro assay. More particularly, for pneumococcal infection, the host cells from humans are cells from the respiratory tract, including lung epithelial and nasopharyngeal epithelial cells, or venous endothelial cells. Suitable cells and cell lines include, but are not limited to, endothelial cells, lung cells, leukocytes, buccal cells, adenoid cells, skin cells, conjunctivial cells, ciliated cells, and other cells representative of infected organs. As demonstrated in an example, infra, a human umbilical vein endothelial cell (HUVEC) line, which is available from Clonetics (San Diego, Calif.), can be used. In another example, infra, lung Type II alveolar cells, which can be prepared as described in Example 2 or can be obtained as a cell line available from the American Type Culture Collection (ATCC) under accession number ATCC A549, are used. Alternatively, adherence to human monocyte-derived macrophages, obtained from blood, can be tested. Other target cells, especially for S. pneumoniae, are oropharynlgeal cells, such as buccal epithelial cells [Andersson et al., Microb. Pathogen. 4:267–278 (1988); J. Exp. Med. 158:559–570 (1983); Infect. Iinmun. 32:311–317 (1981)].

Generally, any adherence assay known in the art can be used to demonstrate loss of adhesion due to mutagenesis or contact with a peptide methionine sulfoxide reductase antagonist. One such assay follows: The cells to which adherence is to be assayed are cultured for 4–8 days [Wright and Silverstein, J. Exp. Med. 156:1149–1164 (1982)] and then transferred to Terasaki dishes 24 hours prior to the adherence assay to allow formation of a confluent monolayer [Geelen et al., Infect. Immun. 61:1538–1543 (1993)]. The bacteria are labelled with fluorescein [Geelen et al., 1993, supra], adjusted to a concentration of $5 \times 10^7$ cfu/ml, and added in a volume of 5 µl to at least 6 wells. After incubation at 37° C. for 30 min, the plates are washed and fixed with PBS/glutaraldehyde 2.5%. Attached bacteria are enumerated visually using a fluorescence microscope, such as a Nikon Diaphot Inverted Microscope equipped with epifluorescence.

As exemplified herein, identification of antagonists of the pneumococcal peptide methionine sulfoxide reductase of the invention has important implications for reducing virulence of Gram positive, and indeed, as demonstrated with E. coli, Gram negative bacteria. More particularly, the present invention unexpectedly demonstrates that peptide metlhionine sulfoxide reductase is a adhesion-associated protein in these bacteria, and that knocking out peptide methionine sulfoxide reductase activity (whether by mutation or, as described herein, by identification of an inhibitory or antagonist compound) reduces bacterial adhesion, and thus, virulence. In a specific embodiment, infra, an antagonist of pneumococcal peptide methionine sulfoxide reductase of the invention can be used to block adherence of the Gram positive bacterium Neisseria gonorrhoea; in another specific embodiment, the antagonist can be used to block adherence of the Gram positive bacterium E. coli.

The term "peptide methionine sulfoxide reductase" or "MsrA" is used herein to infer to a bacterial repair enzyme (also called peptide methionine sulfoxide reductase). In a specific embodiment, the peptide methionine sulfoxide reductase of the invention has a deduced amino acid sequence as depicted in SEQ ID NO:2. The term "msrA" refers to a nucleic acid encoding a peptide methionine sulfoxide reductase of the invention. In a specific embodiment, an msrA of the invention has a nucleotide sequence corresponding to the sequence depicted in SEQ ID NO:1.

A "virulence protein" is any bacterial product required for bacterial survival within an infected host. Thus, virulence determinants are attractive drug discovery candidates since neutralization of a virulence determinant can reduce the virulence of the bacteria.

An "adhesion associated protein" as used herein refers to a protein that is indirectly involved in adherence of bacteria to target cells, such as endothelial cells or lung cells. As such, the term "adhesion associated protein" includes proteins that may have other functional activities, such as motility, signal transduction, cell wall assembly, or macromolecular transport. An "adhesin" is a protein found on the surface of a cell, such as a bacterium, that is directly involved in adherence, and thus effects some degree of adherence or adhesion to another cell. Of particular importance to the present invention are adhesins of Gram positive bacteria that promote adhesion to eukaryotic cells, i.e., that are involved in bacterial virulence. Adhesins, in order to be effective in promoting adherence, should be surface proteins, i.e., be accessible at the surface of the cell. However, an peptide methionine sulfoxide reductase need not, and probably is not, located at the surface of the cell.

Abbreviations: LC, type II lung epithelial cells; EC, human vein endothelial cells; MsrA, peptide methionine sulfoxide reductase; RBC, guinea pig erythrocytes A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

In its primary aspect, the present invention concerns the discovery that bacterial peptide methionine sulfoxide reductases are important for maintaining bacterial adhesins. The invention further relates to the identification and isolation of a gene encoding a peptide metlhionine sulfoxide reductase in pneumococci.

In particular, the invention concerns pneumococcal peptide methionine sulfoxide reductase (SEQ ID NO:2), encoded by msrA (SEQ ID NO:1), various peptide methionine sulfoxide reductases of *S. pneumoniae* which demonstrates activity in the maintenance of adhesins.

The nucleotide sequence of the genes can be used to prepare oligonucleotide probes or primers for polymerase chain reaction (PCR) for diagnosis of infection with a particular strain or species of Gram positive bacterium, particularly to confirm diagnosis of virulent *S. pneumoniae*.

Alternatively, the protein can be used to immunize an appropriate animal to generate polyclonal or monoclonal antibodies, as described in detail below. Such antibodies can be used in immunoassays to diagnose infection with a particular strain or species of bacteria, or to evaluate the level of expression of peptide methionine sulfoxide reductase as it may relate to bacterial virulence. Thus, peptide methionine sulfoxide reductases can be used to generate species-specific antibodies for diagnosis of infection with that species. In a specific aspect, the species of bacterium is *S. pneumoniae*.

Isolation of Genes for Peptide methionine sulfoxide reductase

The present invention provides msr cDNA and corresponding gene fragments that can be used to obtain the full length gene encoding pneumococcal or other homologous Gram positive peptide methionine sulfoxide reductases.

In accordance with the present invention there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual," Second Edition (1989) Cold Spring Harbor Laboratory Press, Cold Spring Harbor, N. Y. (herein "Sambrook, et al., 1989"); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below. A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

The term "viral vector" refers to a virus containing a recombinant nucleic acid, whereby the virus can introduce the recombinant nucleic acid to a cell, i.e., the virus can transform the cell. According to the present invention, such vectors may have use for the delivery of a nucleic acid-based vaccine, as described herein.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. Preferably a minimum length for a hybridizable nucleic acid is at least about 10 nucleotides; more preferably at least about 15 nucleotides.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that directs the host cell to translocate the polypeptide to the cell surface or secrete the polypeptide into the media, and this signal peptide is selectively degraded by the cell upon exportation. Signal sequences can be found associated with a variety of proteins native to prokaryotes and eukaryotes.

In a further embodiment, screening for genes encoding exported adhesion associated proteins can be performed on PhoA-positive transformants by testing for loss of adherence of a Gram positive bacterium to a primary cell or a cell line to Adhesion assays.

Generally, the invention also provides for identification of a functional property of a protein produced by an peptide methionine sulfoxide reductase gene by comparing the homology of the deduced amino acid or nucleotide sequence to the amino acid sequence of a known protein, or the nucleotide sequence of the gene encoding the protein.

Any Gram positive bacterial cell can potentially serve as the nucleic acid source for the molecular cloning of an msrA gene homologous to the pneumococcal msrA of the invention. The nucleic acid sequences can be isolated from Streptococcus, Bacillus, Mycobacterium, Staphylococcus, Enterococcus, and other Gram positive bacterial sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired msrA gene may be accomplished in a number of ways. For example, if an amount of a portion of a gene or a fragment thereof is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). Those DNA fragments with substantial homology to the probe will hybridize. The present invention provides specific examples of DNA fragments that can be used as hybridization probes for pneumococcal exported proteins. These DNA probes can be based, for example, on SEQ ID NO:1. Alternatively, the screening technique of the invention can be used to isolate additional gene fragments for use as probes.

It is also possible to identify the appropriate fragment by restriction enzyme digestion(s) and comparison of fragment sizes with those expected according to a known restriction map if such is available. Further selection can be carried out on the basis of the properties of the gene.

As described above, the presence of the gene may be detected by assays based on the physical, chemical, or immunological properties of its expressed product. For example DNA clones that produce a protein that, e.g., has similar or identical electrophoretic migration, isoelectric focusing behavior, proteolytic digestion maps, proteolytic activity, antigenic properties, or functional properties, especially adhesion-associated activity. In a specific example, infra, the ability of a pneumococcal peptide methionine sulfoxide reductase protein to maintain adhesins is demonstrated by inhibition of adhesion when the protein is mutated.

Alternatives to isolating the genomic DNA include, but are not limited to, chemically synthesizing the gene sequence itself from a known sequence that encodes an MsrA. For example, DNA cloning of a gene can be isolated from Gram positive bacteria by PCR using degenerate oligonucleotides. Other methods are possible and within the scope of the invention.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. In a preferred aspect of the invention, the msrA coding sequence is inserted in an E. coli cloning vector. Other examples of vectors include, but are not limited to, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated.

In specific embodiments, transformation of host cells with recombinant DNA molecules that incorporate the isolated gene or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The present invention also relates to vectors containing genes encoding analogs and derivatives of peptide methionine sulfoxide reductases that have the same functional activity as pneumococcal peptide metlhionine reductase. The production and use of derivatives and analogs related to an peptide methionine sulfoxide reductase are within the scope of the present invention. In a specific embodiment, the derivative or analog is functionally active, i.e., capable of exhibiting one or more functional activities associated with a full-length, wild-type peptide methionine sulfoxide reductase. As one example, such derivatives or analogs demonstrate adhesin maintenance activity. In another embodiment, such derivatives or analogs show peptide methionine sulfoxide reductase activity.

In particular, derivatives can be made by altering encoding nucleic acid sequences by substitutions, additions or deletions that provide for functionally equivalent molecules. Due to the degeneracy of nucleotide coding sequences, other DNA sequences which encode substantially the same amino acid sequence as an peptide methionine sulfoxide reductase gene may be used in the practice of the present invention. These include but are not limited to nucleotide sequences comprising all or portions of an peptide methionine sulfoxide reductase genes that are altered by the substitution of different codons that encode the same amino acid residue within the sequence, thus producing a silent change. Likewise, the peptide methionine sulfoxide reductase derivatives of the invention include, but are not limited to, those containing, as a primary amino acid sequence, all or part of the amino acid sequence of an peptide methionine sulfoxide reductase including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, truptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such conservative amino acid substitutions will not be expected to significantly alter apparent molecular weight or isoelectric point of the protein.

The genes encoding peptide methionine sulfoxide reductase derivatives and analogs of the invention can be produced by various methods known in the art. The manipulations which result in their production can occur at the gene or protein level. For example, a cloned gene sequence can be modified by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of an peptide methionine sulfoxide reductase, care should be taken to ensure that the modified gene remains within the same translational reading frame as the peptide methionine sulfoxide reductase gene, uninterrupted by translational stop signals, in the gene region where the desired activity is encoded.

Additionally, the nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis [Hutchinson, C., et al., *J. Biol. Chem.* 253:6551 (1978); Zoller and Smith, *DNA* 3:479–488 (1984); Oliphant et al., *Gene* 44:177 (1986); Hutchinson et al., *Proc. Natl. Acad. Sci.* U.S.A. 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Expression of a Peptide Methionine Sulfoxide Reductase

The gene coding for peptide methionine sulfoxide reductase, or a functionally active fragment or other derivative thereof, can be inserted into an appropriate expression vector, i.e., a vector which contains the necessary elements for the transcription and translation of the inserted protein-coding sequence. An expression vector also preferably includes a replication origin. The necessary transcriptional and translational signals can also be supplied by the native gene and/or its flanking regions. A variety of host-vector systems may be utilized to express the protein-coding sequence. Preferably, however, a bacterial expression system is used to provide for high level expression of the protein with a higher probability of the native conformation. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination).

Expression of nucleic acid sequence encoding an peptide methionine sulfoxide reductase or peptide fragment may be regulated by a second nucleic acid sequence so that the exported protein or peptide is expressed in a host transformed with the recombinant DNA molecule. For example, expression of peptide methionine sulfoxide reductase may be controlled by any promoter/enhancer element known in the art, but these regulatory elements must be functional in the host selected for expression. For expression in bacteria, bacterial promoters are required. Eukaryotic viral or eukaryotic promoters, including tissue specific promoters, are preferred when a vector containing an peptide methionine sulfoxide reductase gene is injected directly into a subject for transient expression, resulting in heterologous protection against bacterial infection, as described in detail below. Promoters which may be used to control peptide methionine sulfoxide reductase gene expression include, but are not limited to, prokaryotic expression vectors such as the β-lactamase promoter [Villa-Kamaroff, et al., *Proc. Natl. Acad. Sci. U.S.A.* 75:3727–3731 (1978)], or the tac promoter [DeBoer, et al., *Proc. Natl. Acad. Sci. U.S.A.* 80:21–25 (1983)]; [see also "Useful proteins from recombinant bacteria" in Scientific American, 242:74–94 (1980)].

Expression vectors containing peptide methionine sulfoxide reductase gene inserts can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR with incorporation of radionucleotides or stained with ethidium bromide to provide for detection of the amplified product. In the second approach, the presence of a foreign gene inserted in an expression vector can be detected by nucleic acid hybridization using probes comprising sequences that are homologous to an inserted msrA gene. In the third approach, the recombinant vector/host system can be identified and selected based upon the presence or absence of certain "marker" gene functions (e.g., β-galactosidase activity, PhoA activity, thymidine kinase activity, resistance to antibiotics, transformation phenotype, occlusion body formation in baculovirus, etc.) caused by the insertion of foreign genes in the vector. If the gene is inserted within the marker gene sequence of the vector, recombinants containing the msrA insert can be identified by the absence of the marker gene function. In the fourth approach, recombinant expression vectors can be identified by assaying for the activity of the gene product expressed by the recombinant. Such assays can be based, for example, on the physical or functional properties of the gene product in in vitro assay systems, e.g., peptide methionine sulfoxide reductase enzymatic activity.

Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda); and plasmid and cosmid DNA vectors, to name but a few. The choice of vector will depend on the desired use of the vector, e.g., for expression of the protein in prokaryotic or eukaryotic cells.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered exported protein may be controlled. Furthermore, different host cells have characteristic and specific mechanisms for the translational and post-translational processing and modification (e.g., cleavage of signal sequence) of proteins. Appropriate cell lines or host systems can be chosen to ensure the desired modification and processing of the foreign protein expressed. Different vector/host expression systems may effect processing reactions, such as proteolytic cleavages, to a different extent.

Preparation of Antibodies to Peptide methionine sulfoxide reductase

According to the invention, recombinant peptide methionine sulfoxide reductase, and fragments or other derivatives or analogs thereof, or cells expressing the foregoing may be used as an immunogen to generate antibodies which recognize the peptide methionine sulfoxide reductase. Such antibodies include but are not limited to polyclonal, monoclonal, chimeric, single chain, Fab fragments, and an Fab expression library.

Various procedures known in the art may be used for the production of polyclonal antibodies to peptide methionine sulfoxide reductase, or derivative or analog thereof. For the production of antibody, various host animals can be immunized by injection with the recombinant peptide methionine sulfoxide reductase, or a derivative (e.g., fragment) thereof, including but not limited to rabbits, mice, rats, etc. In one embodiment, the recombinant MsrA or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward an peptide methionine sulfoxide reductase, or analog thereof, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for an MsrA together with genes from a human antibody molecule of appropriate biological activity can be used; such antibodies are within the scope of this invention. Such human or humanized chimeric antibodies are preferred for use in passive immune therapy (described infra), since the human or humanized antibodies are much less likely than xenogenic antibodies to induce an immune response, in particular an allergic response, themselves.

According to the invention, techniques described for the production of single chain antibodies (U.S. Pat. No. 4,946, 778) can be adapted to produce MsrA-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for an MsrA or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked imnmunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The foregoing antibodies can be used in methods known in the art relating to the localization and activity of an peptide methionine sulfoxide reductase, e.g., for Western blotting, imaging, measuring levels thereof in appropriate physiological samples, etc.

Diagnosis of a Gram Positive Bacterial Infection

The antibodies of the present invention that can be generated against peptide methionine sulfoxide reductase from Gram positive bacteria, particularly pneumococcus, are valuable reagents for the diagnosis of an infection with a Gram positive microorganism, particularly pneumococcus. In particular, antibodies to specific peptide methionine sulfoxide reductases of the invention may be valuable for detection and diagnosis of pneumococcal infection. Presently, diagnosis of infection with a Gram positive bacterium is difficult. According to the invention, the presence of Gram positive bacteria in a sample from a subject suspected of having an infection with a Gram positive bacterium can be detected by detecting binding of an antibody to an exported protein to bacteria in or from the sample. In one aspect of the invention, the antibody can be specific for an epitope on peptide methionine sulfoxide reductase characteristic of an allele in a unique strain or a limited number of strains of the bacterium, thus allowing for diagnosis of infection with that particular strain (or strains). Alternatively, the antibody can be specific for many or all strains of a bacterium, thus allowing for diagnosis of infection with that species. In a specific embodiment, the species is S. pneumoniae.

Diagnosis of infection with a Gram positive bacterium can use any immunoassay format known in the art, as desired. Many possible immunoassay formats are described in the section entitled "Preparation of Antibodies to Peptide methionine sulfoxide reductases". The antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

Alternatively, the nucleic acids and sequences thereof of the invention can be used in the diagnosis of infection with a Gram positive bacterium. For example, the msrA genes or hybridizable fragments thereof can be used for in situ hybridization with a sample from a subject suspected of harboring an infection of Gram positive bacteria. In another embodiment, specific gene segments of a Gram positive bacterium can be identified using PCR amplification with probes based on the msrA genes of the invention. In one aspect of the invention, the hybridization with a probe or with the PCR primers can be performed under stringent conditions, or with a sequence specific for a unique strain or a limited number of strains of the bacterium, or both, thus allowing for diagnosis of infection with that particular strain (or strains). Alternatively, the hybridization can be under less stringent conditions, or the sequence may be homologous in any or all strains of a bacterium, thus allowing for diagnosis of infection with that species. Preferably the bacterium is S. pneumoniae.

Identification and isolation of a gene encoding peptide methionine sulfoxide reductase of the invention provides for expression of the protein in quantities greater than can be isolated from natural sources, or in indicator cells that are specially engineered to indicate the activity of a receptor expressed after transfection or transformation of the cells. According, in addition to rational design of agonists and antagonists based on the structure of peptide methionine sulfoxide reductase, the present invention contemplates an alternative method for identifying specific ligands of peptide methionine sulfoxide reductase using various screening assays known in the art.

Any screening technique known in the art can be used to screen for peptide methionine sulfoxide reductase agonists or antagonists. The present invention contemplates screens for small molecule ligands or ligand analogs and mimics, as well as screens for natural ligands that bind to and agonize or antagonize, preferably antagonize, peptide methionine sulfoxide reductase in vivo.

Knowledge of the primary function of the enzyme, and the similarity of enzyme with enzymes of known function, or more importantly, for which inhibitory agents are known, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists, and are made possible by the ability to overexpress large quantities of the protein.

Another approach uses recombinant bacteriophage to produce large libraries. Using the "phage method" [Scott and Smith, Science 249:386–390 (1990); Cwirla, et al., Proc. Natl. Acad. Sci. USA, 87:6378–6382 (1990); Devlin et al., Science, 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the recent method of Fodor et al. [*Science* 251:767–773 (1991)] are examples. Furka et al. [*14th International Congress of Biochemistry*, Volume 5, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., "Generation and screening of an oligonucleotide encoded synthetic peptide library," *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for peptide methionine sulfoxide reductase ligands according to the present invention.

The screening can be performed with recombinant cells that express the peptide methionine sulfoxide reductase, or alternatively, using purified receptor protein, e.g., produced recombinantly, as described above. For example, the ability of labeled, soluble or solubilized peptide methionine sulfoxide reductase that includes the ligand-binding portion of the molecule, to bind ligand can be used to screen libraries, as described in the foregoing references.

The present invention will be better understood from a review of the following illustrative description presenting the details of the constructs and procedures that were followed in its development and validation.

EXAMPLE 1

GENETIC IDENTIFICATION OF ADHESION-ASSOCIATED PROTEINS IN *STREPTOCOCCUS PNEUMONIAE*

A strategy was developed to mutate and genetically identify putative exported proteins in *Streptococcus pneumoniae* by coupling the technique of mutagenesis with gene fusions to phoA. Vectors were created and used to screen pneumococcal DNA in *Escherichia coli* and *S. pneumoniae* for translational gene fusions to alkaline phosphatase (PhoA). This study identified several genetic loci that encode putative exported proteins. By similarity to the derived sequences from other genes from prokaryotic organisms these loci probably encode proteins that play a role in signal transduction, macromolecular transport and assembly, maintaining an intracellular chemiosmotic balance and nutrient acquisition.

PhoA[+] pneumococcal mutants were isolated and the loci from one of these mutants showed similarity to Neisseria PilB as described in International Patent Publication No. WO 95/06732, published Mar. 9, 1995, U.S. application Ser. No. 08/116,541, filed Sep. 1, 1993, and U.S. application Ser. No. 08/245,511, filed May 18, 1994.

Materials and Methods

The materials and methods for this example were described in detail in International Patent Publication No. WO 95/06732, published Mar. 9, 1995, U.S. application Ser. No. 08/116,541, filed Sep. 1, 1993, and U.S. application Ser. No. 08/245,511, filed May 18, 1994.

Strains and media. Strains of *S. pneumoniae* and their relevant characteristics generated in this study are listed in Table 1 of International Patent Application No. WO95/06732.

*S. pneumoniae* were plated on tryptic soy agar supplemented with sheep blood (TSAB) to a final concentration of 3% (vol./vol.); grown in a liquid semi synthetic casein hydrolysate medium supplemented with yeast extract (C+Y medium) [Lacks and Hotchkiss, *Biochem. Biophys. Acta.* 39:508–517 (1960)]; or in some instances, grown in Todd Hewitt broth (THBY) supplemented with yeast to a final concentration of 5% (w/v).

Recombinant DNA techniques. Plasmids pHRM100 and pHRM104 (FIG. 1) were constructed as described previously.

The mutagenesis strategy in *S. pneumoniae* involved insert duplication upon plasmid integration (FIG. 1B). Because of this duplication there was a low frequency excision of the integrated plasmid with its insert that contaminated chromosomal preparations of pneumococcal DNA. Therefore, integrated plasmids containing a pneumococcal insert were easily recovered from *S. pneumoniae* by transformation of these excised plasmids directly into competent *E. coli*.

Results and Discussion

Identification of exported proteins by sequence analysis of the PhoA fusions from *S. pneumoniae*. The plasmids containing pneumococcal inserts were recovered in *E. coli* from pneumococcal mutants that displayed the blue phenotype on XP. Digestion of these plasmids with KpnI dissects the pneumococcal inserts from the parent vector. The size of the inserts were all approximately 400 to 900 base pairs.

Exp 3 from SPRU 40 showed significant sequence similarity to PilB from *N. gonorrhoeae* [Taha et al., EMBO J. 7:4367–4378 (1988)]. There were two regions of similarity which correspond to the C-terminal domain of PilB. There was a short gap of 25 amino acids for Exp3 and 37 amino acids for PilB which showed no similarity. This suggests a modular structure function relationship for these two proteins. Consistent with this result, PhoA-PilB hybrids were localized to the membrane fraction of *N. gonorrhoea* [Taha et al., *Mol. Microbiol* 5:137–48 (1991)] indicating membrane translocation. Partial nucleotide sequence information and deduced amino acid sequence information for Exp 3 were described previously in International Patent Publication WO 95/06732, published Mar. 9, 1995, and in U.S. application Ser. No. 08/116,541, filed Sep. 1, 1993, and U.S. application Ser. No. 08/245,511, filed May 18, 1994.

EXAMPLE 2

PEPTIDE METHIONINE SULFOXIDE REDUCTASE CONTRIBUTES TO THE MAINTENANCE OF ADHESINS

This example reports that peptide methionine sulfoxide reductase (MsrA), a repair enzyme, contributes to the maintenance of adhesins in *Streptococcus pneumoniae, Neisseria gonorrhoea*, and *Escherichia coli*. A screen of a library of pneumococcal mutants for loss of adherence uncovered a MsrA mutant with 75% reduced binding to GalNAβ1-4Gal containing eucaryotic cell receptors which are present on type II lung cells and vascular endothelial cells. Subsequently it was shown that an *E. coli* MsrA mutant displayed decreased type I fimbriae-mediated, mannose-dependent, agglutination of erythrocytes. Previous work [Taha, M. K.

et. al. EMBO J. 7:4367–4378 (1988)] had shown that mutants with defects in the pilA–pilB locus from *Neisseria gonorrhoea* were altered in their production of type IV pili. The data presented here shows that pneumococcal MsrA and gonococcal PilB expressed in *E. coli* have MsrA activity. Together these data suggest that MsrA is required for the proper expression or maintenance of functional adhesins on the surfaces of these three major pathogenic bacteria.

To define the nature of the ligands on the surface of pneumococcus responsible for binding to eucaryotic cells, a library of mutants with defects in exported proteins was screened for the inability to bind to the various eucaryotic receptors (Example 1). One mutant showed decreased binding to the GalNAc$\beta$1-4Gal class of receptors. The gene disrupted in this mutant was shown by sequence similarity to encode a protein with homologs in several bacteria including *E. coli* (MsrA), *N. gonorrhoea* (PilB), *Haemophilus influenzae* [Fleischmann, et al., 1995, supra], and *Mycoplasma genitalium* [Fraser et al., *Science*, 270: 397–403 (1995)] and the eucaryotic organism *C. elegans* [Wilson et al. *Nature* 369:32–38 (1994)]. The characteristics of MsrA, a protein that reduces methionine sulfoxide residues in proteins, have been extensively studied [Brot et al., *Proc Natl. Acad. Sci. USA* 78:2155–2158 (1981); Brot and Weissbach, *Arch. Biochem. Biophys.*, 223, 271–281 (1993); Brot and Weissbach, in *The Chemistry of Sulphones and Sulphoxides*, p. 851–872 (1988); Abrams et al., *Proc. Natl. Acad. Sci. USA* 78:7483–7486 (1981)]. In the present study it is demonstrated that PilB, which is implicated in pili production, and the pneumococcal protein have enzyme activity. In addition, an *E. coli* msrA mutant also exhibits a reduced mannose-dependenit ability to bind to receptors on eukaryotic cells. Based on these observations we propose that the MsrA is critical for the production and or the maintenance of the functional properties of adhesins in the major bacterial pathogens, notably *E. coli, N. gonorrhoea* and *S. pneumoniae*.

Materials and Methods

Strains, bacterial growth and molecular genetics. The pneumococcal strain used in this study was R6x, which is a derivative of the noncapsulated Rockefeller University strain R36A [Taraby and Fox, *Proc. Natl. Acad. Sci. USA,* 70:3541–3545 (1973)]. *S. pneumoniae* were routinely plated on tryptic soy agar (Difco) supplemented with sheep blood (Micropure Medical Inc., White Bear Lake, Minn.) to a final concentration of 3% (v/v). Liquid cultures of pneumococcus were grown in a semi-synthetic casein hydrolysate medium supplemented with a yeast extract [Lacks, *Biochem. Biophys.* Act 39:508–517 (1960)]. For the selection and maintenance of pneumococci containing chromosomally integrated plasmids, bacteria were grown in the presence of 0.5 $\mu$g/ml erythromycin.

The *E. coli* strains used in these studies were MC 1061 and SK 8779 (msrAl::kan). The latter is a mutant strain of MC1061 carrying a disrupted msrA gene [Moskovitz et al., *J. Bacteriol* 177:502–507, (1995)].

Established protocols were used for the genetic transformation of pneumococci as well as the recovery of spontaneously excised plasmids [Pearce et al., *Mol. Microbiol,* 9:1037–1050 (1993); Pearce et al., *Mol. Microbiol.* 12:881–892 (1994); Pearce et al., *J. Bacteriol,* 177:86–93 (1994)]. Mutant libraries of pneumococci containing the non-replicating chromosomally integrated plasmids pHRM100 and pHRM104 were created as previously described (Pearce et al., 1993, supra).

For hemagglutination studies, *E. coli* strains were grown in Luria broth (LB) under static conditions for 48–72 h. To maintain plasmids in mutant strains, ampicillin and/or kanamycin (50 $\mu$g/ml) were added to the culture medium.

Bacterial adherence. The assays for the adherence of pneumococci to LC, EC, and immobilized glycoconjugates were performed as previously described [Cundell and Tuomanen, 1994, supra]. The glycoconjugates used to detect binding specificities for the disaccharides GalNAc$\beta$1-4Gal (asialo-GM1 and asialo-GM2), GalNAc$\beta$1-3Gal (globoside), or the PAF receptor ($\alpha$1-acid glycoprotein) were purchased from Sigma Chemical Co. (St. Louis, Mo.).

The assays for the adherence of gonococci to epithelial cells were performed with A431 cells (ATCC CRL 1555). These cells were grown in DMEM (GIBCO) supplemented with 10% heat-inactivated fetal calf serum at 37° C. in a humidified 5% $CO_2$ atmosphere. Cells were grown in 24-well treated tissue culture plates to near confluence ($10^5$ cells/well). Gonococci were grown 18–20 h on GCB with Kellogg's supplements, swabbed into GCB agar (Difco), and diluted to appropriate density in DMEM. A431 cells were infected at an MOI of 10. After 7 h incubation, non-adherent bacteria were removed by washing 5× with sterile PBS. Cells were lifted with PBS+0.5 mM EDTA and appropriate dilutions were plated immediately onto GCB plates. Total bacterial counts were determined by removing the supernatant, lifting the cells, and plating dilutions of this mixture.

Hemagglutination. Agglutination of guinea pig erythrocytes was used as an assay for type I fimbriae-mediated, mannose-dependent adherence to eucaryotic cell receptors. Serial dilutions of bacterial suspensions of *E. coli* were mixed with an equal volume of 2% guinea pig erythrocytes (Micropure Medical Inc., White Bear Lake, Minn.). The titer of hemagglutinationl was determined as the dilution exhibiting no visible agglutination after 2 h incubation at 4° C. In some assays, $\alpha$-methyl-D-mannoside was added to inhibit hemagglutination [Neeser et al., *Infect. Immun.,* 52:428–436 (1986); Giampapa et al., *J. Biol. Chem.* 263:5362–5367 (1988)].

DNA manipulations. Most procedures were performed according to standard methods [Sambrook et al., *Molecular Cloning: A Laboratory Manual* (1989)]. The recovery of integrated plasmids harboring pneumococcal DNA from mutant strains of pneumococcus into *E. coli* has been described elsewhere [Pearce et al. (1993) supra; Pearce et al., (1994) supra].

The genetic locus containing the pneumococcal msrA gene, as well as adjacent DNA, was obtained by inverse PCR. A plasmid (pTW1) harboring a 600 bp sequence of pneumococcal DNA from the adhesion defective mutant SPRU40 was established in *E. coli* and the entire sequence of this insert was determined. Outward facing primers were designed to the ends of this DNA. Chromosomal DNA from the parent strain, R6x, was digested with EcoRI, self-ligated, and then amplified by the PCR using the primers to the insert from prW1. Conditions for the PCR were 94° C. for 1 min for denaturing, 55° C. for 1 min for annealing, and 72° C. for 2 min for extension, for 25 cycles. A single 3.5 kb product was obtained and sequenced with primers specific to this amplified product. DNA sequence was determined by the Taq dye terminator cycle sequencing method on an automated DNA sequencer (model 373, Applied Biosystems) operated by the Protein/DNA Technology Center at Rockefeller University. Derived protein sequences were analyzed for similarity to sequences deposited in the database at the National Center for Biotechnology Information (Washington, D.C.) using the BLAST algorithm [Altshul et al., *J. Mol. Biol.* 215:403–410 (1990)]. Alignments were performed with the PILEUP program available on version 7 of the Genetics Computer Group (University of Wisconsin) sequence analysis software package [Devereux et al., 1984, supra].

Enzyme activity. MsrA activity was determined as previously described using 150 pmol of N-acetyl-[$^3$H]-methionine sulfoxide as substrate [Brot et al., *Anal. Biochem.* 122:291–294 (1982)]. Cell free extracts of *S. pneumoniae* were prepared by sonicatioii of a suspension of mid-log phase bacteria in the presence of glass beads in phosphate buffered saline (PBS) containing 2 mM phenyl-methylsulfonyl fluoride. The extract was centrifuged at 32,000×g for 20 min and the supernatant assayed for enzymatic activity. *E. coli* cell free extracts were obtained by sonication of a cellular suspension as described previously [Moskowitz et al., 1995, supra]. Following centrifugation, the supernatants were analyzed for enzyme activity.

MsrA and PilB expression in *E. coli*. The gene for the pneumococcal msrA was synthesized by the PCR using a 5' sense primer containing an EcoRI site (5'-ATAAAGATG GAATTCATTTATCTAGCA-GGTTGG)(SEQ ID NO:3) and a 3' reverse complement primer with an added Xba1 restriction site (5'-CCCTTCTATTCATAT TCTAGAAATGAAG)(SEQ ID NO:4). The pilB gene was also made by the PCR using a 5' sense primer containing an EcoRI site (5'-CATCAAAATG GAATTCCGTACTTTCTTTTCCC)(SEQ ID NO:5) and a 3' reverse complement primer with an added Xba1 site (5'-CCGGGTTAGGTCTAGATG-CGGCTTATTTCAC)(SEQ ID NO:6). The PCR was performed for 30 cycles of 30 sec at 94° C., 60 sec at 50° C, and 90 sec at 72° C., using chromosomal *S. pneumoniae* DNA or *N. gonorrhoea* DNA. The pTrc99A vectors harboring the pneumococcal msrA and pilB genes were denoted as pJM300, and pJM400, respectively. *E. coli* mutant cells lacking the msrA gene [Moskowitz et al., 1995, supra]were transformed with an aliquot of each ligation mixture, and grown in LB containing ampicillin and kanamycin (50 μg/ml each) to an $A_{600}$ of 0.4. Isopropyl thiogalactopyranoside (IPTG) was then added to a final concentration of 1 mM and the bacteria cultured for an additional 4 h. Bacteria were collected by centrifugation, suspended in a buffer containing 25 mM Tris-HCI, pH 7.4, and disrupted by sonication. The lysates were centrifuged and the supernatants were analyzed for MsrA activity [Brot et al., 1982, supra].

Statistics. Data were analyzed using Student's t-test. Results were considered statistically significant at $P<0.05$. Data for the pneumococcal adherence assays is presented as the mean of six individual measurements; the standard deviation of any value did not vary by greater that 15% of that value.

Results

Figure 2A:
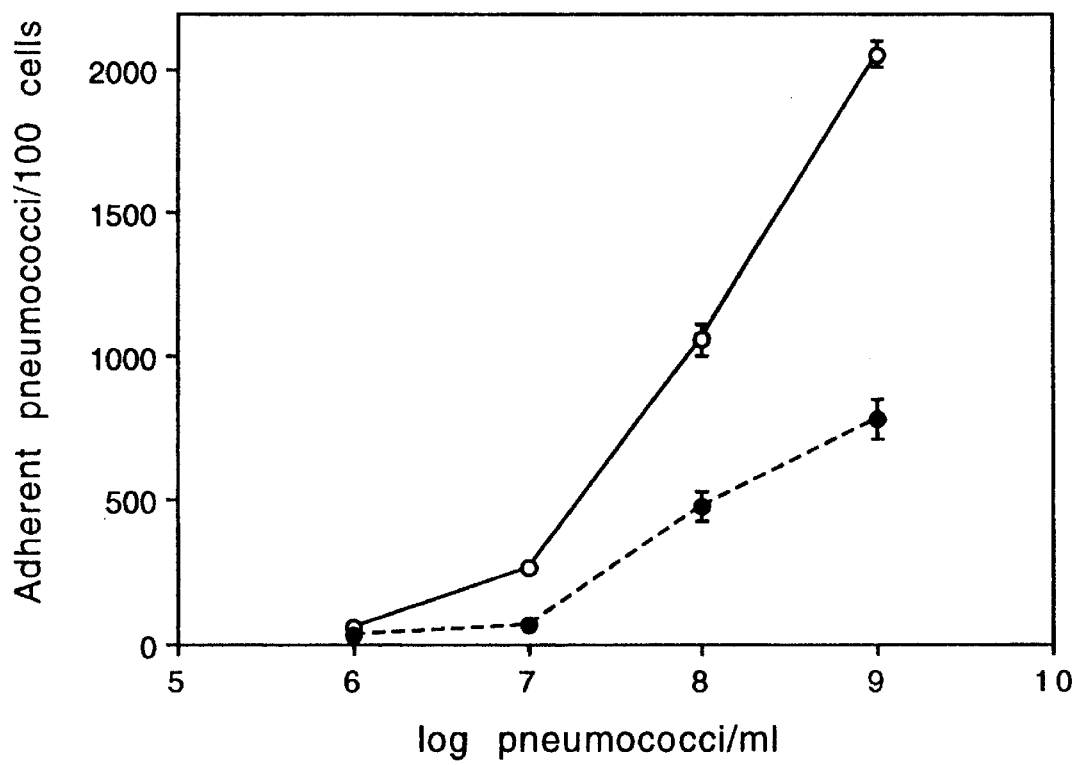
FIG. 2. Adherence of R6x (open circles) and SPRU40 (closed circles) to LC (A) and EC (B). Adherence was determined microscopically as the number of attached fluorescein-labeled bacteria per 100 eucaryotic cells. Data are the mean ± SD of 6 experiments. Adherence of SPRU40 to both LC and EC was significantly reduced (P<0.05) at $10^7$ to $10^9$ cfu/ml, compared to the parent strain R6x.
Figure 2B:
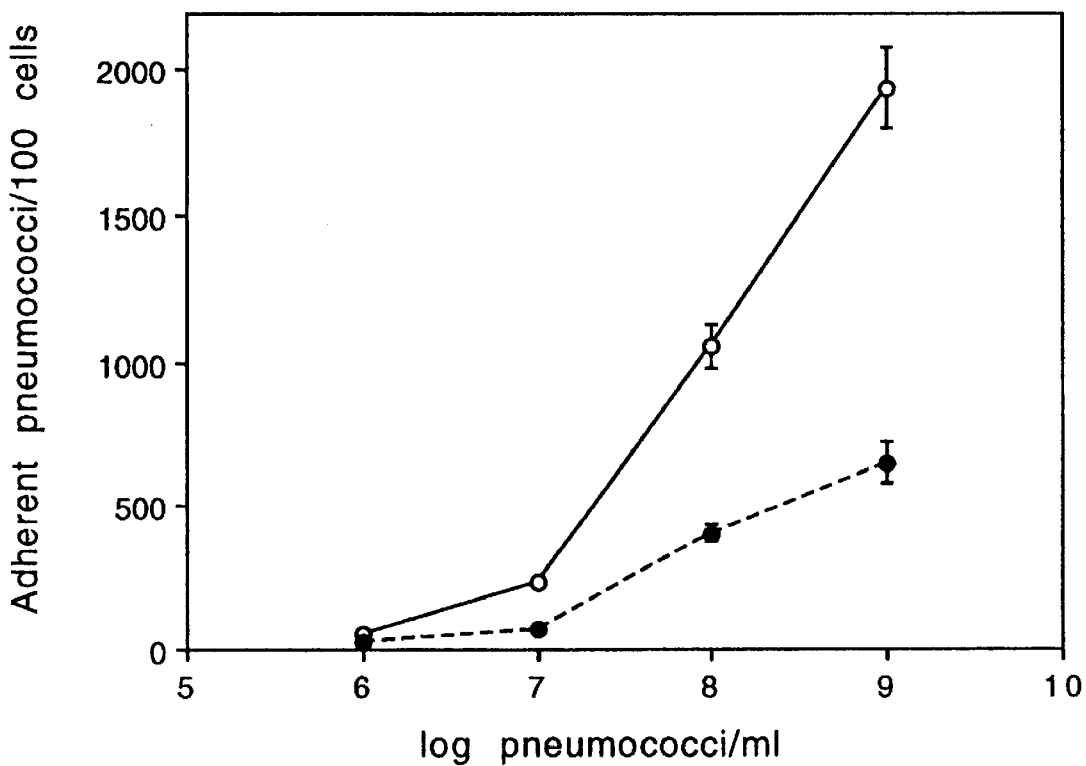
Figure 3:
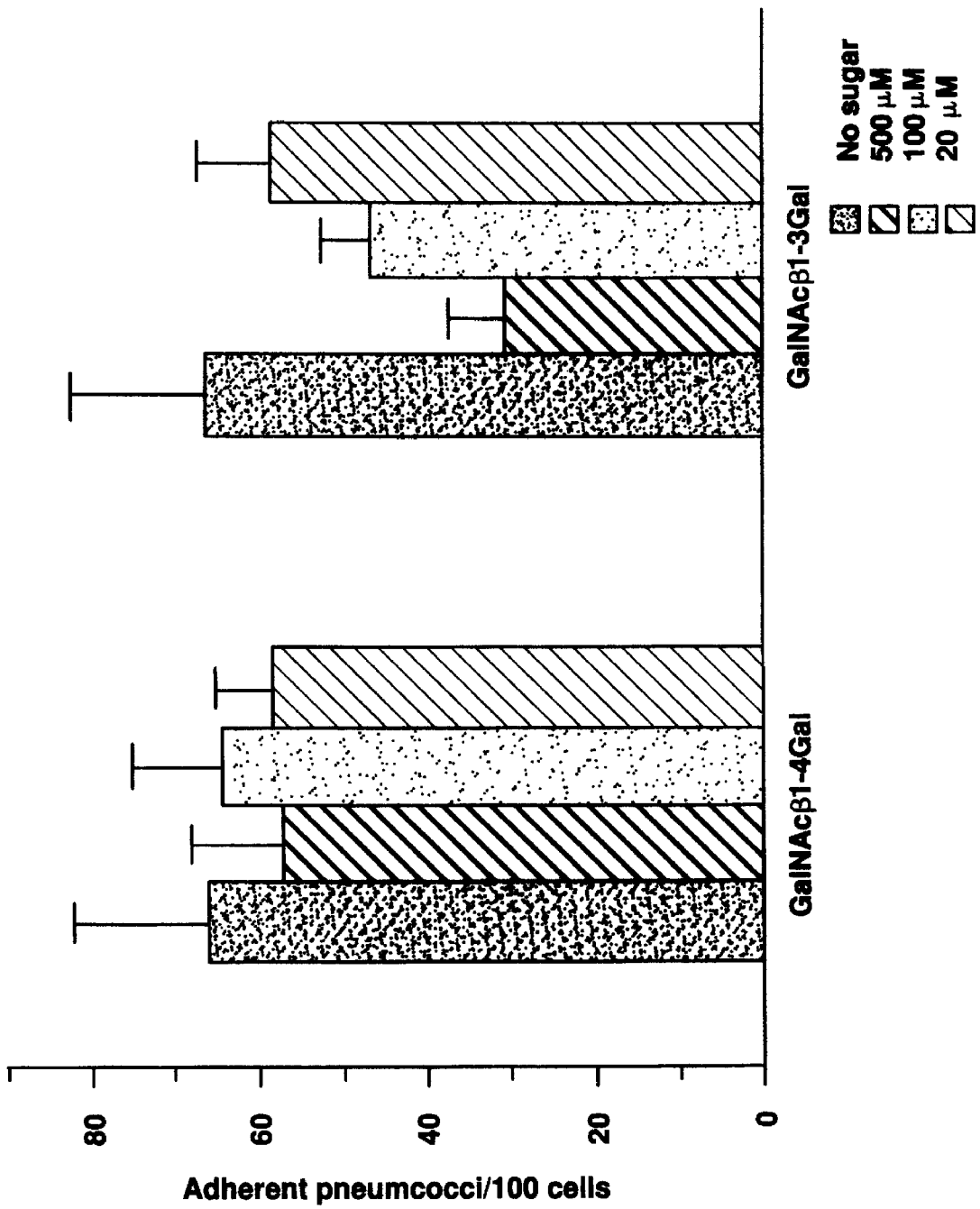
FIG. 3. Effect of glycoconjugates on adherence of pneumococci to LC. R6x were incubated with asialo-GM1, a GalNAcβ1-4Gal containing glycoprotein, or globoside, a GalNAcβ1-3Gal containing glycoprotein for 15 min prior to addition of the bacteria to the LC monolayer. Adherence was determined microscopically as the number of attached fluorescein-labeled bacteria per 100 LC. Data are the mean ± SD of 6 experiments. Adherence of SPRU40 to LC was significantly reduced (P<0.05) by pre-incubation with 100 and 500 µM GalNAcβ1-3 Gal, compared to control (no sugar).

Identification of a pneumococcal adherence deficient mutant. Initially, a bank of mutants with defects in exported proteins was generated by insertion duplication mutagenesis with two phoA (alkaline phosphatase) fusion vectors described elsewhere (Pearce et al., 1993, supra]. Mutants positive for alkaline phosphatase activity (150) were screened for loss of adherence to eukaryotic cells or to glycoconjugates that were determined to best represent the eucaryotic cellular receptors for pneumococcus [Cundell and Tuomanen, (1994) supra; Krivan et al., *Proc. Natl. Acad. Sci. USA* 85:6157–6161 (1988); Anderson et al., *J. Exp. Med.*, 158:559–570 (1983)]. One mutant, SPRU40, showed reduced adherence to LC and EC (FIG. 2). To confirm that the loss of adherence was the result of the marked mutation, the allele from SPRU40 was recovered and genetically transferred to the parent strain and a similar loss of adherence was observed (data not shown). Residual binding of SPRU40 to LC was inhibited by an exogenous glycoconjugate containing the disaccharide GalNAcβ1-3Gal, while a glycoconjugate containing GalNAcβ1-4Gal had no effect on residual binding (FIG. 3). A similar pattern of glycoconjugate mediated inhibition was observed in adherence assays between pneumococci and EC (data not shown). In further studies, the ability to adhere directly to immobilized glycoconjugate analogs was assessed. The binding of SPRU40 to glycoconjugates containing GalNAcβ1-4Gal was reduced 75% compared to the parent strain, while binding to other glycoconjugates was unchanged (Table 1). These data suggest that the locus disrupted in SPRU40 is required for the production of a functional ligand that binds to the GalNAcβ1-4Gal receptor present on eucaryotic cells.

TABLE 1

Direct adherence of pneumococci to immobilized glycoconjugates

| Strain | Adherent bacteria/0.0625 mm$^2$ | | | |
|---|---|---|---|---|
| | No sugar | GalNAcβ1-4Gal | GalNAcβ1-3Gal | PAF receptor |
| R6x | 27 ± 7 | 398 ± 63 | 161 ± 16 | 162 ± 17 |
| SPRU40 | 32 ± 10 | 103 ± 15* | 158 ± 15 | 165 ± 21 |

Pneumococci (10$^7$ CFU/ml) were incubated with immobilized GalNAcβ1-4Gal (asialo-GM2, 100 μM), GalNAcβ1-3Gal (globoside, 100 μM) or PAF receptor (α1-acid glycoprotein, 100 μM) for 30 min at 37° C. Data are the mean ± SD of 6 experiments.
*Significantly less ($P < 0.05$) than adherence by the parent strain, R6x.

Sequence analysis of the locus disrupted in SPRU40. Recovery and analysis of the altered locus in SPRU40 showed a gene consisting of 936 bases which would encode a protein of 312 amino acids with a predicted molecular mass of 35 kDa (FIG. 3). A potential ribosome binding site was found 15 bases upstream from the ATG initiation codon and a potential transcription terminator 4 bases downstream from the TAA stop codon. Comparison of the derived amino acid sequence to entries in the current DNA sequence libraries revealed several homologs. The deduced amino acid sequence of the pneumococcal gene displayed >40% identity with MsrA from *E. coli* [Rahmani et al., *J. Biol. Chem.*, 267:15549–15551 (1992)] (SEQ ID NO:8) and 50% identity with the carboxy-terminal region of PilB from *N. gonorrhoea*, a putative transcriptional regulator [Taha et al., EMBO *J.* 7:4367–4378 (1988)] (SEQ ID NO:9). Within the amino-terminal region of PilB there is a domain which contains a close match to the consensus sequence CysGlyProCys which is the active site for protein oxidoreductases found in thioredoxin and thioredoxin-like proteins. This region is most like the domains found in a putative disulfide exchange protein (DsbE) from *Haemophilus influenzae* [Fleischmann et al., 1995, supra] and thioredoxin and thioredoxin like proteins from *Rhodobacter sphaerodies* [Pile et al., 1990, supra; Vargas et al., *J. Bacteriol,* 176:4117–23 (1994)]. None of these homologs suggested that the pneumococcal gene encoded a structural element that serves as an adhesin. Since, as shown below, we demonstrate that MsrA activity is associated with the protein product of this gene, it is designated msrA after its *E. coli* counterpart.

Upstream of the pneumococcal msrA, in the opposite orientation, are four conserved DNA sequences with >90% identity to the consensus sequences for several pneumococcal BOX elements [Martin et al., *Nucleic Acids Res.*, 20:3479–3483 (1992)]. These sequences have the potential to form stem-loop structures and it has been proposed that they function as regulatory elements. Upstream from the start codon (29 bp) of msrA is one copy of Box A followed by two copies of Box B, and one copy of Box C.

Figure 4A:
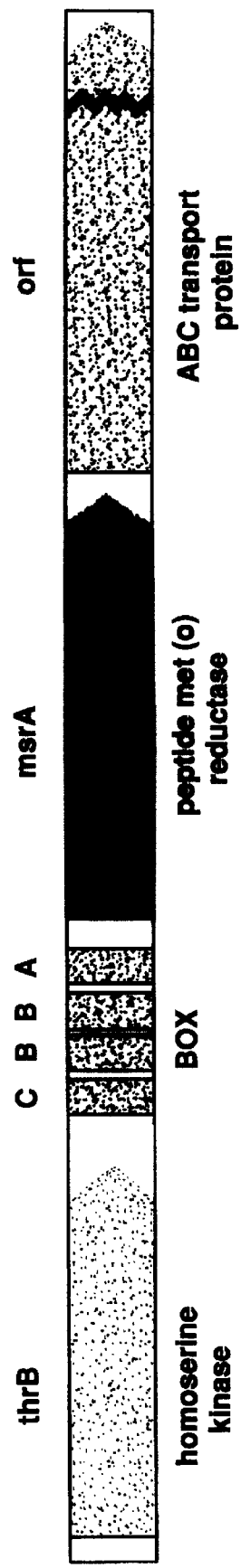
FIG. 4. Structural organization and sequence analysis of the pneumococcal msrA. (A) Structural organization of the pneumococcal msrA and adjacent DNA. (B) Sequence alignment of the pneumococcal MsrA (pMsrA) (SEQ ID NO:2) with PilB (SEQ ID NO:7) and the *E. coli* MsrA (SEQ ID NO:8). A conserved domain corresponding to the active site of protein oxido-reductases present in PilB, DsbE, a disulfide exchange protein from *Haemophilus influenzae* [Fleischmann, R. D., et. al. *Science,* 269:496–512 (1995)], and TrxA from *Rhodobacter spheroides* [Pile et al., *J Bacteriol,* 172:1556–1561 (1990)] is also indicated. Sequence alignment was performed with the PILEUP program available on version 7 of the Genetics Computer Group (University of Wisconsin) sequence analysis software package [Devereux, *Nucleic Acids Res.,* 12:387–395 (1984). Identical or conserved amino acids are indicated (uppercase). A consensus sequence was derived on the basis of a comparison of each individual sequence associated with pneumococcal msrA and alignment of the deduced amino acid sequences of the homologs of the *S. pneumoniae, E. coli,* and *N. gonorrhoea* MsrA.

Adjacent to msrA are two genetic elements that potentially express gene products with homologs in other bacteria (FIG. 4A). Upstream of the BOX region is a homolog of the homoserine kinase (thrB) from *Bacillus subtilis* [Parsot, EMBO J., 5:3013–3013 (1986)]. In this organism, this enzyme is the fourth component of five enzymes required for threoninie biosynthesis. The biosynthetic pathways for lysine, methionine and isoleucine diverge from the threonine biosynthetic pathway. Downstream of msrA is a member of the ABC family of transporters required for the active transport of many diverse molecules across lipid membranes [for a review see Higgins, *Annu. Rev. Cell. Biol.* 8:67–113 (1992)]. This homolog is most like HlyB found in many bacteria which is dedicated to the secretion of hemolysins across bacterial membranes. We note that the hallmark ATP binding motif or "Walker" box found in all of these homologs is also present in the deduced amino acid sequence of the pneumococcal gene [Higgins et al., *Nature* 323:448–50 (1986)].

Figure 5:
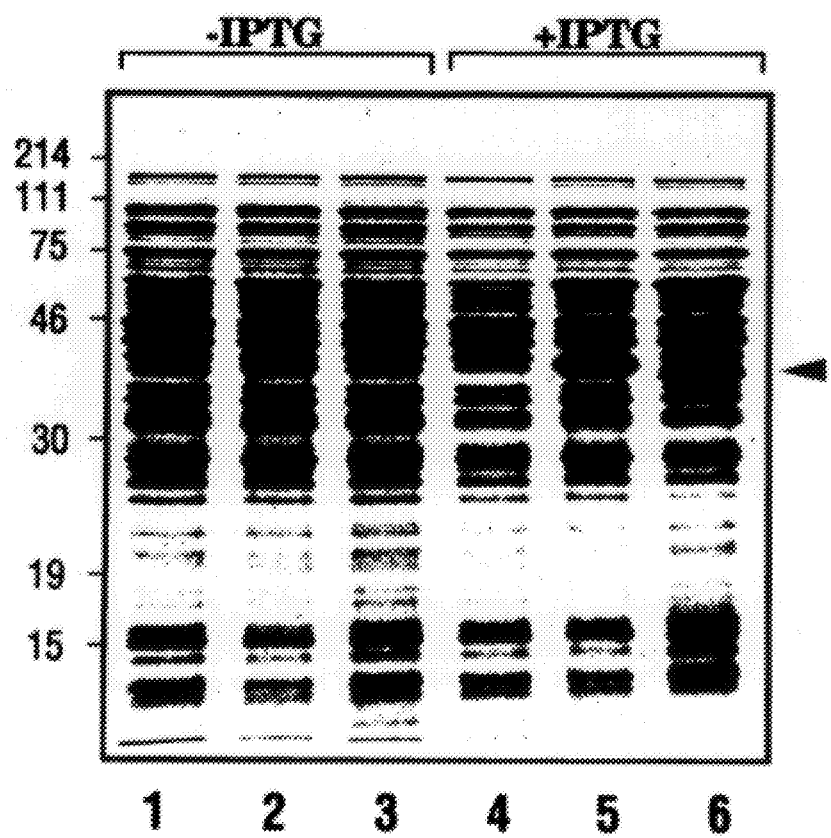
FIG. 5. Expression of MsrA and PilB. The genes for PilB and pneumococcal MsrA were cloned into the pTrc99A expression vector just down stream of an IPTG inducible promoter and the corresponding plasmids transformed into SK8779 (msrA1::kan). These strains were then grown with or without the addition of the inducer. Lanes 1 and 4; cells transformed with pTrc99A; lanes 2 and 5, cells transformed with pJM300 (msrA); lanes 3 and 6, cells transformed with pJM400 (pilB).

Peptide methionine sulfoxide reductase activity associated with MsrA and PilB. Experimental data showed that the *E. coli* MsrA, a homolog of the pneumococcal MsrA, is an enzyme that reduces methionine sulfoxide residues to methionine [Rahman et al., 1992, supra; Rahman et al., *Cell. Mol. Biol.* 38:529–542 (1992)] while other data suggested that PilB, the homolog from *N. gonorrhoea*, is a sensor component of the two component family of sensor regulators (Taha et al., 1988, supra; Taha et al., *J. Bacteriol.* 174:5978–5981 (1992)]. We undertook a series of experiments to resolve this incongruity. First, compared to extracts of the parent pneumococcal strain which had a MsrA specific activity of 0.34 pmol/h/µg protein, there was no detectable MsrA activity associated with the pneumococcal strain SPRU40 which harbors a disrupted msrA. This result, in addition to the sequence similarity between the two genes, suggested that the pneumococcal msrA encodes a MsrA. Second, the pneumococcal msrA and pilB were expressed in *E. coli* under the control of an inducible promoter harbored on appropriate expression vectors and these strains were assessed for MsrA activity. The host strain for these vectors was an msrA mutant which has no MsrA enzyme activity. These cells were then grown in the presence or absence of the inducer, IPTG. FIG. 5 shows that only in the presence of IPTG were two proteins of about 35 kDa and 32 kDa synthesized (lanes 2 vs. 5 and 3 vs. 6) in cells transformed with the plasmids bearing the pneumococcal msrA and pilB, respectively. The molecular weight of the expressed pneumococcal protein is in good agreement with its predicted molecular weight from the deduced amino acid sequence. The induced protein from the strains harboring pilB is smaller than its predicted molecular mass of 58 kDa [Taha et al., 1988, supra]. It is possible that this is a proteolytic product of PilB.

In order to determine whether the expression of these proteins correlated with MsrA activity, the cells harboring the inducible pneumococcal msrA and pilB genes were assayed for this activity. Table 2 shows that in the absence of IPTG there was no enzyme activity in any of the transformants. After the addition of IPTG only strains harboring the inducible msrA (pJM300) and pilB (pJM400) genes produced MsrA activity. Finally, a gene fusion between pneumococcal msrA and glutathione transferase was constructed, the protein product purified and shown to have MsrA activity (11.1 pmol/h/µg protein). Therefore, we conclude that pneumococcal MsrA and gonococcal PilB are homologs of *E. coli* MsrA and that all three possess MsrA enzyme activity.

TABLE 2

Expression of pneumococcal MsrA and PilB in an *E. coli* MsrA mutant

| Plasmid | MsrA Specific Activity (pmol N-acetyl met/h/µg) | |
| --- | --- | --- |
| | −IPTG | +IPTG |
| pTrc99A | 0.00 | 0.00 |
| pJM300 | 0.00 | 4.44 |
| pJM400 | 0.00 | 6.50 |

The construction of the plasmids, expression of the msrA and pilB genes, and the MsrA enzyme assay are as described in the Materials and Methods.

Peptide peptide methionine sulfoxide reductase affects *E. coli* mediated hemagglutination. Mutants with defects in the pilA–pilB locus are altered in levels of pilin expression, while pneumococcal mutants with defects in msrA have alterations in surface ligands responsible for binding to eucaryotic cell receptors. Therefore, we tested MsrA defective *E. coli* strains for changes in binding to eucaryotic cell receptors using a model system for the ability of *E. coli* that express type I fimbriae to agglutinate erythrocytes in a mannose-dependent manner. An 8-fold decrease in hemagglutinationi was observed for an msrA defective *E. coli* strain. Hemagglutination of the mutant was restored to the levels observed in the parent strain with the introduction of a plasmid containing msrA expressed from its own promoter [Rahman et al., 1992, supra]. The activity restored by the plasmid correlated with α-methyl-D-mannoside inhibitable hemagglutination, consistent with type I fimbriae (Table 3).

TABLE 3

Effect of MsrA on hemagglutination by *E. coli*

| Strain | MsrA Enzyme Activity | Hemagglutination Activity | Conc. (µg/ml) α-Me-D-mannoside for inhibition* |
| --- | --- | --- | --- |
| Parent MC1061 | + | 1:16 | 250 |
| SK8779 | − | 1:2 | 30 |
| SK8779 plasmid carrying msrA | + | 1:16 | 125 |

Data presented are a representative experiment of five similar experiments.
*Minimal concentration required for complete inhibition.
Dilution of *E. coli* at which visible hemagglutination was lost.

Peptide peptide methionine sulfoxide reductase affects adherence of *N. gonorrhoeae* to eucaryotic cells. It was previously shown that a *N. gonorrhoeae* pilB mutant was hyperpiliated [Taha et at., 1988, supra], which might suggest a hyperadherent phenotype. In adherence assays at an MOI (multiplicity of infection) of 10, 88% of pilB mutant genococci adhered to A431 epithelial cells, compared to 34% of wild type gonococci. Adherence of non-piliated derivatives of wild type and pilB mutant strains were reduced to 0.24 and 0.23% respectively. This demonstrates that hyperpiliated gonococci with a defect in pilB are also hyperadherent.

Discussion

The functional properties of the molecules on the surfaces of microbial pathogens and host cells are essential to defining the molecular characteristics of an infectious disease. Many elements are required for the expression, assembly, positioning and maintenance of these surface molecules. In the effort to characterize the adherence properties of *S. pneumoniae* to eucaryotic cells [Cundell et at., 1995, supra; Cundell et al., 1995, supra; Weiser et al., *Infect Immun*, 62, 2582–2589 (1994); Cundell, et al., *Infect Immun*, 63, 757–761 (1995)], several pneumococcal elements that contribute to the process of adherence have been defined [Cundell et al., 1995, supra]. To date no specific surface proteins have been shown to function as adhesins in pneumococcus although several membrane associated molecules contribute to the expression of adlhesins [Cundell et al., (1995) supra]. Using a strategy that couples bacterial mutagenesis to an in vitro adherence assay we identified an adhesion deficient mutant with a defect in a gene, designated msrA, that codes for an enzyme, a peptide methionine sulfoxide reductase, that may function to maintain the functional properties of a pneumococcal adhesin. It has been shown that *S. pneumoniae* recognizes several specific glycoconjugates on the surfaces of LC and EC [Cundell and Tuomanen, 1994, supra; Krivan et al., 1988, supra]. The pneumococcal msrA defective mutant displayed substantially decreased adherence to LC and EC as a result of a lack of recognition of the specific GalNAcβ1-4Gal ligand.

The oxidation state of sulfur-containing amino acids affects the functional properties of many proteins and both procaryotic and eucaryotic organisms have enzymes that alter the redox state of these amino acids. Thioredoxin, glutaredoxin and protein disulfide isomerases are examples of intracellular proteins that have been shown to be required for the maintenance of functional properties of a wide variety of proteins (for a review see [Homgren, A. *J. Biol. Chem.*, 264:13963–13966 (1989)]. A growing family of dedicated protein disulfide oxido-reductases have been characterized in a variety of bacteria. One class of enzymes catalyzes the oxidation of cysteine residues promoting correct inter and intra molecular disulfide bond formation, thus conveying functionality to these proteins [Missiakas et al., *Proc Natl Acad Sci USA*, 90:7084–8 (1993); Missiakas et al., *Embo J*, 13:2013–20 (1994); Kamitani et al., EMBO J., 11:57–67 (1992); Bardwell et al., *Cell*, 67:581–589 (1991)] [for a recent review see Freedman et al., *TIBS*, 19:331–35 (1994)]. It has been shown that these enzymes are required for the correct folding and enzymatic properties of the exported protein, alkaline phosphatase, from *E. coli* [Kamintani et al., 1992, supra; Bardwell et al. 1991, supra) and the secretion of a variety of virulence determinants in *Vibrio cholerae*, including a colonization factor and presumed adlhesin [Peek and Taylor *Proc Natl Acad Sci USA*, 89:6210–4 (1992)]. An example of these enzymes has also been shown to be required for the process of natural transformation in *H. influenzae* [Tomb, *Proc Natl Acad Sci USA*, 89:10252–6 (1992)].

A second class of enzyme, MsrA, catalyzes the reversible oxidation-reduction of methionine sulfoxide in proteins to methionine [Brot and Weissbach, 1988, supra]. The pneumococcal msrA gene product expressed in *E. coli* has MsrA activity. The oxidation of methionine in proteins has been shown to result in loss of biological activity, which is restored by MsrA [Brot and Weissbach, 1988, supra]. This seems to be the most likely molecular mechanism responsible for affecting the production of the adhesins associated with the bacteria presented in the current study. Methionine in proteins may be oxidized by biologically reactive oxygen intermediates such as hydrogen peroxide and superoxide anion. Pathogenic bacteria are challenged by these molecules as the products of normal bacterial metabolism [Dupuy et al., *J Biol Chem*, 3739–43 (1992); Ma and Eaton, *Proc Natl Acad Sci USA*, 89:7924–8 (1992)] or as toxins produced by the host's immune defense cells [Beamon and Beaman, *Ann Rev Microbiol*, 38:27–48 (1984); Christman et al., *Cell*, 41:753–762 (1985)]. It is of note that pneumococcus is a catalase-deficient organism and is particularly susceptible to reactive oxygen intermediates.

The results of a search of the most recent genetic and protein databases revealed homologs of the pneumococcal MsrA in *E. coli, N. gonorrhoeae* (PilB), *H. influenzae* [Fleishmann et al., 1995, supra], *M. genitalium* [Fraser et al., 1995, supra] and *C. elegans* [Wilson et al., 1994, supra]. To explore a link between this enzyme and other bacterial adhesins, the adherence properties of a type I fimbriated *E. coli* msrA defective mutant was analyzed. The absence of functional MsrA in type I fimbriated *E. coli* resulted in decreased mannose-dependent agglutination of erythrocytes. This suggests that MsrA is required for the production or maintenance of surface fimbriae on this pathogen. Electron microscopy of the *E. coli* strains revealed no apparent phenotypic differences in the fimbriae of the msrA defective mutants and parent strains (data not shown). FimH, present at the tip of the fimbriae, has been implicated as the specific molecule responsible for this type of adherence [Jones et at., *Proc. Natl. Acad. Sci. USA*, 92:2081–2085 (1995)]. Immunogold labeling of the mutant and the parent strain revealed no apparent differences in quantity or distribution of FimH (data not shown). Therefore, the affect of MsrA on the maintenance of this adhesin was not revealed by this type of analysis.

PilB is the best characterized element associated with the production of an adhesin associated with the bacteria considered in this study. Originally discovered as part of a regulatory element (pilA–pilB), it was shown that the gene products of this locus control transcription of pil E. Pil E is the expression locus for pilin, the major protein submit of gonococcal pili [Taha et al., 1988, supra; Taha et al., 1992]. It has been proposed that PilA–PilB are similar to the two component family of sensor regulators [Taha et al., 1992; Taha et al., *Mol. Microbiol.*, 5:137–148 (1991); Taha and Giorgini, *Mol. Microbiol*, 15:667–77 (1995). Experimental data supports the notion that PilA is the response regulator of this system and controls pilin expression at the level of transcription in a manner dependent on the novel GTPase activity associated with this protein [Arvidson and So, *J Biol Chem*, 270:26045–26048 (1995); Arvidson and So, *J Bacteriol*, 177:2497–2504 (1995)]. The model proposes that PilB functions as the sensor kinase of this system that phosphorylates PilA to alter its ability to affect pilin transcription [Taha et al., 1992, supra; Taha et al., 1991, supra; Taha and Giorgini, 1995, supra].

This Example shows that recombinant PilB has MsrA activity and that the N-terminal region contains a domain highly similar to the active site (CysGlyProCys) associated with thioredoxin-like proteins. It is of note that this is the first example of a single protein that contains both thioredoxin-like and reductase domains. If, as originally proposed, PilB acts in concert with PilA to regulate the expression of pilE, it may not be by the traditional phosphorelay system common to two component sensor regulators. Recent data from in vitro studies showed that PilB was not phosphorylated and there was no exchange of phosphate with PilA [Taha and Giorgini, 1995, supra]. Therefore, we propose that PilB may affect the transcription of pilE by the inherent oxido-reductase activity of the protein by affecting the transcriptional activity function of PilA. This is not without precedent. In the face of strong oxidants, a series of stress response elements are up regulated by the transcription factor NF-κB in eucaryotic cells [Meyer et al., Embo J, 12:2005–15 (1993)] and it has been shown that thioredoxin directly affects NF-κB mediated gene transcription by reduction of a disulfide bond in this transcription factor [Matthews et al., Nucleic Acids Res, 20:3821–30 (1992); Schenk et al., Proc Natl Acad Sci USA, 91:1672–6 (1994). As an alternative mechanim, since PilB has been shown to be an exported, membrane associated protein, this protein may function to maintain the oxidative state of PilE or the many support proteins required for the assembly of pillin.

Mutants of N. gonorrhoeae with defects in pilB have previously been shown to be hyperpiliated [Taha et al., 1988, supra], as well as hyper-adherent (this manuscript) which is in contrast to the E. coli and pneumococcal mutants with defects in MsrA homologs that are adhesion deficient. Since the targets for the MsrA activities in these bacteria have not been identified we can only speculate on a mechanism of action. It is possible that MsrA homologs may be affecting gene transcription in the case of N. gonorrhoeae while in the other bacteria the mechanism may be at other levels of gene regulation or as a chaperone, maintaining a functional adhesin.

In summary, we have shown that a specific class of enzymes, MsrA, is responsible for the production of functional adhesins on the surfaces of three major bacterial pathogens. From this and other studies it is clear that the oxidative state of the sulfur groups of both methionine and cysteine within proteins contributes to the expression and maintenance of the functional properties of the molecules on the surface of bacteria. Finally, since MsrA serves this critical function for three major pathogens of both gram negative and gram positive types, it appears to be a useful target for anti-infective therapy.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is also to be understood that all base pair sizes given for nucleotides and all molecular weight information for proteins are approximate and are used for the purpose of description.

Various references are cited throughout this specification, each of which is incorporated herein by reference in its entirety.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 2195 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptococcus pneumoniae
        ( B ) STRAIN: R6x ( i x ) FEATURE:
        ( A ) NAME/KEY: CDS
        ( B ) LOCATION: 1200..2138
        ( D ) OTHER INFORMATION: /codon_start= 1
            / product= "peptide methionine sulfoxide reductase"
            / gene= "msrA"

( i x ) FEATURE:
        ( A ) NAME/KEY: CDS
        ( B ) LOCATION: 37..906
        ( D ) OTHER INFORMATION: /codon_start= 1
            / product= "homoserine kinase homolog"

/ gene= "thrB"

( x i ) SEQUENCE DESCRIPTION: SEQ ID NO:1:

| | | | | | |
|---|---|---|---|---|---|
| ACCTCTTGAA | TACCTTCAAG | GTGCTAGGAG | AATAAGATGA | AGATTATTGT | ACCTGCAACC   60 |
| AGTGCCAATA | TCGGGCCAGG | TTTTGACTCG | GTCGGTGTAG | CTGTAACCAA | GTATCTTCAA  120 |
| ATTGAGGTCT | CCGAAGAACG | AGATGAGTGG | CTGATTGAAC | ACCAGATTGG | CAAATGGATT  180 |
| CCACATGACG | AGCGTAATCT | CTTGCTCACA | ATCGCTTTGC | AAATTGTACC | AGACTTGCAA  240 |
| CCAAGACGCT | TGAAAATGAC | CAGTGATGTC | CCTTTGGCGC | GCGGTTTGGG | TTCTTCCAGC  300 |
| TCGGTTATCG | TTGCTGGGAT | TGAACTAGCC | AACCAACTGG | GTCAACTCAA | CTTATCAGAC  360 |
| CATGAAAAAT | TGCAGTTAGC | GACCAAGATT | GAAGGGCATC | CTGACAATGT | GGCTCCAGCC  420 |
| ATTTATGGTA | ATCTCGTTAT | TGCAAGTTCT | GTTGAAGGGC | AAGTCTCTGC | TATCGTAGCA  480 |
| GACTTTCCAG | AGTGTGATTT | TCTAGCTTAC | ATTCCAAACT | ATGAATTACG | TACTCGCGAC  540 |
| AGCCGTAGTG | TCTTGCCTAA | AAAATTGTCT | TATAAGGAAG | CTGTTGCTGC | AAGTTCTATC  600 |
| GCCAATGTAG | CGGTTGCTGC | CTTGTTGGCA | GGAGACATGG | TGACCGCTGG | GCAAGCAATC  660 |
| GAGGGAGACC | TCTTCCATGA | GCGCTATCGT | CAGGACTTGG | TAAGAGAATT | TGCGATGATT  720 |
| AAGCAAGTGA | CCAAAGAAAA | TGGGGCCTAT | GCAACCTACC | TTTCTGGTGC | TGGGCCGACA  780 |
| GTTATGGTTC | TGGCTTCTCA | TGACAAGATG | CCAACAATTA | AGGCAGAATT | GGAAAAGCAA  840 |
| CCTTTCAAAG | GAAAACTGCA | TGACTTGAGA | GTTGATACCC | AAGGTGTCCG | TGTAGAAGCA  900 |
| AAATAAAGAA | TAGAATATAG | GATGGGAACT | CTTGACCAGA | GGGGTTCATA | TCCTTTTTGT  960 |
| GGAAAGAAGT | TTATACTCAA | TGAAAATCAA | AGAGCAAACT | AGGAAGCTAG | CCGCAGGCTG 1020 |
| CTCCAAACAG | TGTTTTGAGG | TTGTGGATAG | AACTGACGAC | GTCAGCTCAA | GACACTGTTT 1080 |
| TGAGGTTGCA | GATAGAACTG | ACGAAGTCAG | TAACCATACC | CACGGTAAGG | TGACGCTGAC 1140 |
| GTGGTTTGAA | GAGATTTTCG | AAGAGTATTA | GTTAAAAACG | TGATAAGGA | GAAATAAAGA 1200 |
| TGGCAGAAAT | TTATCTAGCA | GGTGGTTGTT | TTTGGGGCCT | AGAGGAATAT | TTTTCACGCA 1260 |
| TTTCTGGAGT | GCTAGAAACC | AGTGGTGGCT | ACGCTAATGG | TCAAGTCGAA | ACGACCAATT 1320 |
| ACCAGTTGCT | CGAGGAAACA | GACCATGCAG | AGGCGGTCCG | AGTGATTTGC | GATGAGAAGG 1380 |
| GAGTGTCACT | CAGAGAGATT | TTACTTTATT | ATTTCCGAGT | TATCGATCCT | CTATCTATCA 1440 |
| ATCAACAAGG | GAATGACCGT | GGTCGCCAAT | ATCGAACTGG | GATTTATTAT | CAGGATGAAG 1500 |
| CAGATTTGCC | AGCTATCTAC | ACAGTGGTGC | AGGAGCAGGA | ACGCATGCTG | GGTCGAAAGA 1560 |
| TTGCAGTAGA | AGTGGAGCAA | TTACGCCACT | ACATTCTGGC | TGAAGACTAC | CACCAAGACT 1620 |
| ATCTCAGGAA | GAATCCTTCA | GGTTACTGTC | ATATCGATGT | GACCGATGCT | GATAAGCCAT 1680 |
| TGATTGATGC | AGCAAACTAT | GAAAAGCCTA | GTCAAGAGGT | GTTGAAGGCC | AGTCTATCTG 1740 |
| AAGAGTCTTA | TCGTGTCACA | CAAGAAGCTG | CTACAGAGGC | TCCATTTACC | AATGCCTATG 1800 |
| ACCAAACCTT | TGAAGAGGGG | ATTTATGTAG | ATATTACGAC | AGGTGAGCCA | CTCTTTTTTG 1860 |
| CCAAGGATAA | GTTTGCTTCA | GGTTGTGGTT | GGCCAAGTTT | TAGCCGTCCG | ATTTCCAAAG 1920 |
| AGTTGATTCA | TTATTACAAG | GATCTGAGCC | ATGGAATGGA | GCGAATTGAA | GTTCGTTCTC 1980 |
| GTTCAGGCAG | TGCTCACTTG | GGTCATGTTT | TCACAGATGG | ACCGCGGGAG | TTAGGCGGCC 2040 |
| TCCGCTACTG | TATCAATTCT | GCTTCTTTAC | GCTTTGTGGC | CAAGGATGAG | ATGGAAAAAG 2100 |
| CAGGATATGG | CTATCTATTG | CCTTACTTAA | ACAAATAAAA | CAGAGAGTGG | GGCTTCCCAC 2160 |
| TTTCTTCATT | TCTAGAATAT | GAATAGAAGG | GATTT | | 2195 |

( 2 ) INFORMATION FOR SEQ ID NO:2:

(i) SEQUENCE CHARACTERISTICS:
  (A) LENGTH: 312 amino acids
  (B) TYPE: amino acid
  (C) STRANDEDNESS:
  (D) TOPOLOGY: Not Relevant (ii) MOLECULE TYPE: protein (iii) HYPOTHETICAL: NO (iv) ANTI-SENSE: NO (vi) ORIGINAL SOURCE:
  (A) ORGANISM: Streptococcus pneumoniae
  (B) STRAIN: R6x (xi) SEQUENCE DESCRIPTION: SEQ ID NO:2:

```
Met Ala Glu Ile Tyr Leu Ala Gly Gly Cys Phe Trp Gly Leu Glu
 1               5                  10                  15
Tyr Phe Ser Arg Ile Ser Gly Val Leu Glu Thr Ser Gly Gly Tyr Ala
            20                  25                  30
Asn Gly Gln Val Glu Thr Thr Asn Tyr Gln Leu Leu Glu Glu Thr Asp
        35                  40                  45
His Ala Glu Ala Val Arg Val Ile Cys Asp Glu Lys Gly Val Ser Leu
 50                  55                  60
Arg Glu Ile Leu Leu Tyr Tyr Phe Arg Val Ile Asp Pro Leu Ser Ile
 65                  70                  75                  80
Asn Gln Gln Gly Asn Asp Arg Gly Arg Gln Tyr Arg Thr Gly Ile Tyr
                85                  90                  95
Tyr Gln Asp Glu Ala Asp Leu Pro Ala Ile Tyr Thr Val Val Gln Glu
            100                 105                 110
Gln Glu Arg Met Leu Gly Arg Lys Ile Ala Val Glu Val Glu Gln Leu
        115                 120                 125
Arg His Tyr Ile Leu Ala Glu Asp Tyr His Gln Asp Tyr Leu Arg Lys
130                 135                 140
Asn Pro Ser Gly Tyr Cys His Ile Asp Val Thr Asp Ala Asp Lys Pro
145                 150                 155                 160
Leu Ile Asp Ala Ala Asn Tyr Glu Lys Pro Ser Gln Glu Val Leu Lys
                165                 170                 175
Ala Ser Leu Ser Glu Glu Ser Tyr Arg Val Thr Gln Glu Ala Ala Thr
            180                 185                 190
Glu Ala Pro Phe Thr Asn Ala Tyr Asp Gln Thr Phe Glu Glu Gly Ile
        195                 200                 205
Tyr Val Asp Ile Thr Thr Gly Glu Pro Leu Phe Phe Ala Lys Asp Lys
210                 215                 220
Phe Ala Ser Gly Cys Gly Trp Pro Ser Phe Ser Arg Pro Ile Ser Lys
225                 230                 235                 240
Glu Leu Ile His Tyr Tyr Lys Asp Leu Ser His Gly Met Glu Arg Ile
                245                 250                 255
Glu Val Arg Ser Arg Ser Gly Ser Ala His Leu Gly His Val Phe Thr
            260                 265                 270
Asp Gly Pro Arg Glu Leu Gly Gly Leu Arg Tyr Cys Ile Asn Ser Ala
        275                 280                 285
Ser Leu Arg Phe Val Ala Lys Asp Glu Met Glu Lys Ala Gly Tyr Gly
290                 295                 300
Tyr Leu Leu Pro Tyr Leu Asn Lys
305                 310
```

( 2 ) INFORMATION FOR SEQ ID NO:3:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer"

( i i i ) HYPOTHETICAL: NO ( i v ) ANTI-SENSE: NO ( x i ) SEQUENCE DESCRIPTION: SEQ ID NO:3:

ATAAAGATGG AATTCATTTA TCTAGCAGGT TGG  33

( 2 ) INFORMATION FOR SEQ ID NO:4:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer"

( i i i ) HYPOTHETICAL: NO ( i v ) ANTI-SENSE: NO ( x i ) SEQUENCE DESCRIPTION: SEQ ID NO:4:

CCCTTCTATT CATATTCTAG AAATGAAG  28

( 2 ) INFORMATION FOR SEQ ID NO:5:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer"

( i i i ) HYPOTHETICAL: NO ( i v ) ANTI-SENSE: NO ( x i ) SEQUENCE DESCRIPTION: SEQ ID NO:5:

ATAAAGATGG AATTCATTTA TCTAGCAGGT TGG  33

( 2 ) INFORMATION FOR SEQ ID NO:6:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer"

( i i i ) HYPOTHETICAL: NO ( i v ) ANTI-SENSE: NO ( x i ) SEQUENCE DESCRIPTION: SEQ ID NO:6:

CCGGGTTAGG TCTAGATGCG GCTTATTTCA C  31

5,834,278

37

-continued ( 2 ) INFORMATION FOR SEQ ID NO:7:

( i ) SEQUENCE CHARACTERISTICS:
( A ) LENGTH: 521 amino acids
( B ) TYPE: amino acid
( C ) STRANDEDNESS:
( D ) TOPOLOGY: Not Relevant ( i i ) MOLECULE TYPE: protein ( i i i ) HYPOTHETICAL: NO ( i v ) ANTI-SENSE: NO ( v i ) ORIGINAL SOURCE:
( A ) ORGANISM: Neisseria gonorrheae ( x i ) SEQUENCE DESCRIPTION: SEQ ID NO:7:

```
Met Lys His Arg Thr Phe Phe Ser Leu Cys Ala Lys Phe Gly Cys Leu
1               5                   10                  15

Leu Ala Leu Gly Ala Cys Ser Pro Lys Ile Val Asp Ala Gly Thr Ala
            20                  25                  30

Thr Val Pro His Thr Leu Ser Thr Leu Lys Thr Ala Asp Asn Arg Pro
            35                  40                  45

Ala Ser Val Tyr Leu Lys Lys Asp Lys Pro Thr Leu Ile Lys Phe Trp
    50                  55                  60

Ala Ser Trp Cys Pro Leu Cys Leu Ser Glu Leu Gly Gln Ala Glu Lys
65                  70                  75                  80

Trp Ala Gln Asp Ala Lys Phe Ser Ser Ala Asn Leu Ile Thr Val Ala
                85                  90                  95

Ser Pro Gly Phe Leu His Glu Lys Lys Asp Gly Glu Phe Gln Lys Trp
            100                 105                 110

Tyr Ala Gly Leu Asn Tyr Pro Lys Leu Pro Val Val Thr Asp Asn Gly
            115                 120                 125

Gly Thr Ile Ala Gln Asn Leu Asn Ile Ser Val Tyr Pro Ser Trp Ala
    130                 135                 140

Leu Ile Gly Lys Asp Gly Asp Val Gln Arg Ile Val Lys Gly Ser Ile
145                 150                 155                 160

Asn Glu Ala Gln Ala Leu Ala Leu Ile Arg Asn Pro Asn Ala Asp Leu
                165                 170                 175

Gly Ser Leu Lys His Ser Phe Tyr Lys Pro Asp Thr Gln Lys Lys Asp
            180                 185                 190

Ser Ala Ile Met Asn Thr Arg Thr Ile Tyr Leu Ala Ala Ala Ala Ser
            195                 200                 205

Gly Ala Trp Lys Pro Ile Ser Asn Ala Ser Thr Ala Trp Leu Thr Arg
    210                 215                 220

Tyr Arg Tyr Ala Asn Gly Asn Thr Glu Asn Pro Ser Tyr Glu Asp Val
225                 230                 235                 240

Ser Tyr Arg His Thr Gly His Ala Glu Thr Val Lys Val Thr Tyr Asp
                245                 250                 255

Ala Asp Lys Leu Ser Leu Asp Ile Leu Gln Tyr Tyr Phe Arg Val
            260                 265                 270

Val Asp Pro Thr Ser Leu Asn Lys Gln Gly Asn Asp Thr Gly Thr Gln
            275                 280                 285

Tyr Arg Ser Gly Val Tyr Thr Asp Pro Ala Glu Lys Ala Val Ile
    290                 295                 300

Ala Ala Ala Leu Lys Arg Glu Gln Gln Lys Tyr Gln Leu Pro Leu Val
305                 310                 315                 320

Val Glu Asn Glu Pro Leu Lys Asn Phe Tyr Asp Ala Glu Glu Tyr His
```

-continued

```
                              325                              330                                335
    Gln  Asp  Tyr  Leu  Ile  Lys  Asn  Pro  Asn  Gly  Tyr  Cys  His  Ile  Asp  Ile
                   340                      345                           350

Arg  Lys  Ala  Asp  Glu  Pro  Leu  Pro  Gly  Lys  Thr  Lys  Ala  Ala  Pro  Gln
              355                      360                      365

Gly  Gln  Arg  Leu  Arg  Arg  Gly  Gln  Arg  Ile  Lys  Asn  Arg  Val  Thr  Pro
         370                      375                      380

Asn  Ser  Asn  Ala  Pro  Asp  Arg  Arg  Ala  Ile  Pro  Ser  Asp  Gln  Asn  Ser
    385                      390                      395                           400

Ala  Thr  Glu  Tyr  Ala  Phe  Ser  His  Glu  Tyr  Asp  His  Leu  Phe  Lys  Pro
                   405                      410                           415

Gly  Ile  Tyr  Val  Asp  Val  Val  Ser  Gly  Glu  Pro  Leu  Phe  Ser  Ser  Ala
                   420                      425                           430

Asp  Lys  Tyr  Asp  Ser  Gly  Cys  Gly  Trp  Pro  Ser  Phe  Thr  Arg  Pro  Ile
                   435                      440                           445

Asp  Ala  Lys  Ser  Val  Thr  Glu  His  Asp  Asp  Phe  Ser  Phe  Asn  Met  Arg
         450                           455                      460

Arg  Thr  Glu  Val  Arg  Ser  Arg  Ala  Ala  Asp  Ser  His  Leu  Gly  His  Val
    465                      470                      475                           480

Phe  Pro  Asp  Gly  Pro  Arg  Asp  Lys  Gly  Gly  Leu  Arg  Tyr  Cys  Ile  Asn
                        485                      490                           495

Gly  Ala  Ser  Leu  Lys  Phe  Ile  Pro  Leu  Glu  Gln  Met  Asp  Ala  Ala  Gly
                   500                      505                           510

Tyr  Gly  Ala  Leu  Lys  Gly  Glu  Val  Lys
                   515                      520
```

( 2 ) INFORMATION FOR SEQ ID NO:8:

( i ) SEQUENCE CHARACTERISTICS:
        ( A ) LENGTH: 1270 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli
        ( B ) STRAIN: B ( i x ) FEATURE:
        ( A ) NAME/KEY: CDS
        ( B ) LOCATION: 241..879
        ( D ) OTHER INFORMATION: /codon_start= 1
                / product= "peptide methionine sulfoxide reductase"

( x i ) SEQUENCE DESCRIPTION: SEQ ID NO:8:

```
AAGCTTACAC  AGCATAACTG  TCGGATATAG  CGCACATTTT  CTCCTGAATA  TCCTTTTTTC      60
CTGCCCCTGG  AACGCCGTTA  AACGCGTTAA  CAAAAATCCA  GTAATATGGA  TTAAAAAGAA     120
GACTAAACCC  CAAATATTTC  TTATGTTTTA  CTTTAGACCT  ATTCACGGTG  GTTATTGTGT     180
GCAAATACGC  CTCTTGTTAC  AACCTTAACC  CCAATGACCG  ATTTTCGGGA  GAGCGACACC     240
ATGAGTTTAT  TTGATAAAAA  GCATCTGGTT  TCCCCCGCCG  ATGCCCTGCC  TGGACGTAAC     300
ACCCCGATGC  CCGTAGCCAC  GCTGCATGCG  GTCAACGGTC  ACTCAATGAC  CAATGTACCT     360
GACGGAATGG  AGATTGCCAT  TTTTGCGATG  GGTTGTTTCT  GGGGTGTGGA  GCGTCTGTTC     420
TGGCAGTTAC  CCGGCGTTTA  CAGCACCGCC  GCAGGCTATA  CCGGAGGCTA  TACGCCAAAT     480
```

```
CCGACTTATC  GGGAAGTGTG  CTCCGGTGAT  ACGGGTCATG  CCGAAGCGGT  ACGCATTGTT      540
TACGATCCTT  CCGTCATCAG  CTATGAGCAG  TTGCTACAGG  TATTTGGGA   GAATCACGAT      600
CCCGCCCAGG  GAATGCGTCA  GGGCAATGAC  CACGGCACGC  AGTATCGTTC  AGCGATTTAT      660
CCGCTGACCC  CAGAACAGGA  TGCCGCAGCT  CGCGCCAGTC  TGGAACGTTT  TCAGGCGGCG      720
ATGCTTGCCG  CCGATGATGA  TCGTCACATC  ACCACGGAAA  TCGCTAACGC  CACACCGTTT      780
TATTATGCCG  AAGATGACCA  CCAGCAATAT  CTGCATAAAA  ACCCGTATGG  TTACTGTGGA      840
ATTGGCGGAA  TTGGCGTCTG  TCTGCCACCG  GAAGCATAGC  GTTACGGGTA  CAAATGTAGA      900
TTGTTGATAA  AGTGCGCTTT  ATTTATGCCA  GATGCGGCGT  AAACGCCTTA  CCAGGCCTAC      960
AAAATCCGTC  AAATTCAATA  TATTGCAAGG  ACTGCGTAGG  CCTGATTGGC  ATAGCGCATC     1020
AGGCAGTATT  GCATTTATCA  GCAGTCTGAA  TTTTAACCCT  CTGGCGACTT  TACAGTACCT     1080
TACGCTATAC  TAGCCACTGA  AAATGCCGGT  TCACTTTCTT  CGAATCGGCT  TTCAATGTGT     1140
ATTTCACACA  AATTAATCAA  CTTCCCTTCC  GAGGATCTGG  CCTGAAAGTC  GGATAAGATA     1200
TGTTAAACAG  TATTTAGTC   ATACTCTGCT  TGATCGCTGT  AAGTGCGTTC  TTCTCGATGT     1260
CCGAGATCTC                                                                1270
```

(2) INFORMATION FOR SEQ ID NO:9:

(i) SEQUENCE CHARACTERISTICS:
        (A) LENGTH: 212 amino acids
        (B) TYPE: amino acid
        (C) STRANDEDNESS:
        (D) TOPOLOGY: Not Relevant (ii) MOLECULE TYPE: protein (iii) HYPOTHETICAL: NO (iv) ANTI-SENSE: NO (vi) ORIGINAL SOURCE:
        (A) ORGANISM: Escherichia coli
        (B) STRAIN: B (xi) SEQUENCE DESCRIPTION: SEQ ID NO:9:

```
Met  Ser  Leu  Phe  Asp  Lys  Lys  His  Leu  Val  Ser  Pro  Ala  Asp  Ala  Leu
  1              5                   10                  15

Pro  Gly  Arg  Asn  Thr  Pro  Met  Pro  Val  Ala  Thr  Leu  His  Ala  Val  Asn
                20                  25                  30

Gly  His  Ser  Met  Thr  Asn  Val  Pro  Asp  Gly  Met  Glu  Ile  Ala  Ile  Phe
            35                  40                  45

Ala  Met  Gly  Cys  Phe  Trp  Gly  Val  Glu  Arg  Leu  Phe  Trp  Gln  Leu  Pro
       50                  55                  60

Gly  Val  Tyr  Ser  Thr  Ala  Ala  Gly  Tyr  Thr  Gly  Gly  Tyr  Thr  Pro  Asn
 65                       70                  75                       80

Pro  Thr  Tyr  Arg  Glu  Val  Cys  Ser  Gly  Asp  Thr  Gly  His  Ala  Glu  Ala
                    85                  90                  95

Val  Arg  Ile  Val  Tyr  Asp  Pro  Ser  Val  Ile  Ser  Tyr  Glu  Gln  Leu  Leu
                100                 105                 110

Gln  Val  Phe  Trp  Glu  Asn  His  Asp  Pro  Ala  Gln  Gly  Met  Arg  Gln  Gly
            115                 120                 125

Asn  Asp  His  Gly  Thr  Gln  Tyr  Arg  Ser  Ala  Ile  Tyr  Pro  Leu  Thr  Pro
       130                 135                 140

Glu  Gln  Asp  Ala  Ala  Ala  Arg  Ala  Ser  Leu  Glu  Arg  Phe  Gln  Ala  Ala
145                      150                 155                      160
```

-continued

| | | | | | | | | | | | | | | |
|---|---|---|---|---|---|---|---|---|---|---|---|---|---|---|
| Met | Leu | Ala | Ala | Asp<br>165 | Asp | Asp | Arg | His | Ile<br>170 | Thr | Thr | Glu | Ile<br>175 | Ala | Asn |
| Ala | Thr | Pro | Phe<br>180 | Tyr | Tyr | Ala | Glu | Asp<br>185 | Asp | His | Gln | Gln | Tyr<br>190 | Leu | His |
| Lys | Asn | Pro<br>195 | Tyr | Gly | Tyr | Cys | Gly<br>200 | Ile | Gly | Gly | Ile | Gly<br>205 | Val | Cys | Leu |
| Pro | Pro | Glu<br>210 | Ala | | | | | | | | | | | | |

What is claimed is:

1. An isolated nucleic acid encoding a protein that has the amino acid sequence of SEQ ID NO:2.

2. The isolated nucleic acid of claim 1 having the nucleic acid sequence of SEQ ID NO:1.

3. The isolated nucleic acid of claim 1 which is a DNA.

4. A cloning vector whih comprises the isolated nucleic acid of claim 1.

5. An expression vector which comprises the isolated nucleic acid of claim 1 operatively associated with an expression control sequence.

6. A bacterial cell transfected or transformed with the expression vector of claim 5.

7. A mammalian cell transfected or transformed with the expression vector of claim 5.

8. A method of expressing a protein that has an amino acid sequence SEQ ID NO:2 in an appropriate cell culture medium under conditions that provide for expression of the protein by the bacterial cell.

9. The method of claim 8 further comprising the step of purifying the protein.

* * * * *